United States Patent
Armstrong et al.

(10) Patent No.: US 6,315,792 B1
(45) Date of Patent: Nov. 13, 2001

(54) REMOTELY REMOVABLE COVERING AND SUPPORT

(75) Inventors: Joseph Robert Armstrong; Michael Vonesh, both of Flagstaff, AZ (US)

(73) Assignee: Gore Enterprise Holdings, Inc.

( * ) Notice: Subject to any disclaimer, the term of this patent is extended or adjusted under 35 U.S.C. 154(b) by 0 days.

(21) Appl. No.: 09/436,511

(22) Filed: Nov. 9, 1999

Related U.S. Application Data

(62) Division of application No. 09/098,103, filed on Jun. 15, 1998, now Pat. No. 6,224,627.

(51) Int. Cl.$^7$ ................ A61F 2/06; D04B 9/12
(52) U.S. Cl. ............ 623/1.23; 623/1.12; 623/1.13; 623/1.15; 606/108; 66/81; 383/206
(58) Field of Search ............... 623/1.23, 1.13, 623/1.15, 1.12; 606/108; 66/81; 383/201, 202–206, 209

(56) References Cited

U.S. PATENT DOCUMENTS

| | | | |
|---|---|---|---|
| 4,878,906 | 11/1989 | Lindemann et al. | 623/1 |
| 5,383,892 | 1/1995 | Cardon et al. | 606/198 |
| 5,399,352 | 3/1995 | Hanson | 424/423 |
| 5,405,378 | 4/1995 | Stecker | 623/1 |
| 5,443,496 | 8/1995 | Schwartz et al. | 623/1 |
| 5,449,373 | 9/1995 | Pinchasik et al. | 606/198 |
| 5,465,436 * | 11/1995 | Bleicher | 383/206 |
| 5,545,210 | 8/1996 | Hess et al. | 623/1 |
| 5,545,211 | 8/1996 | An et al. | 623/1 |
| 5,556,414 | 9/1996 | Turi | 606/198 |
| 5,575,818 | 11/1996 | Pinchuk | 623/1 |
| 5,609,605 | 3/1997 | Marshall et al. | 606/191 |
| 5,665,115 | 9/1997 | Cragg | 623/1 |
| 5,674,276 | 10/1997 | Andersen et al. | 623/1 |
| 5,681,346 | 10/1997 | Orth et al. | 606/198 |
| 5,873,906 * | 2/1999 | Lau et al. | 623/1.1 |
| 6,055,350 * | 4/2000 | Brown et al. | 385/100 |
| 6,077,250 * | 6/2000 | Snow et al. | 604/174 |

FOREIGN PATENT DOCUMENTS

| | | |
|---|---|---|
| 2671482 | 7/1992 | (FR) . |
| 97/21402 | 6/1997 | (WO) . |
| 98/27894 | 7/1998 | (WO) . |

\* cited by examiner

*Primary Examiner*—Michael J. Milano
*Assistant Examiner*—Choon P. Koh
(74) *Attorney, Agent, or Firm*—David J. Johns

(57) ABSTRACT

The invention creates a thin tubular multiple filament (film or fiber) structure that can hold high internal pressures. When desired, an extension of the filaments can be pulled in any direction to unfurl the structure. This device is useful for self expanding stent or stent graft delivery systems, balloon dilatation catheters, removable guide wire lumens for catheters, drug infusion or suction catheters, guide wire bundling casings, removable filters, removable wire insulation, removable packaging and other applications.

15 Claims, 24 Drawing Sheets

REMOTELY REMOVABLE COVERING AND SUPPORT

RELATED APPLICATIONS

The present application is a Divisional of U.S. patent application Ser. No. 09/098,103, filed Jun. 15, 1998 now U.S. Pat. No. 6,224,627.

BACKGROUND OF THE INVENTION

1. Field of the Invention

The present invention relates to apparatus and methods for covering devices, such as required when delivering an expandable device, such as an intraluminal stent or graft.

2. Description of Related Art

Stent and stent-graft usage has gained widespread acceptance by radiologists, cardiologists, and surgeons. These devices are being utilized to radially support a variety of tubular passages in the body, including arteries, veins, airways, gastro-intestinal tracts, and biliary tracts. The preferred method of placing these devices has been to use specialized delivery systems to precisely place and deploy a device at the site to be treated. These delivery systems allow the practitioner to minimize the trauma and technical difficulties associated with device placements. Attributes of delivery systems include: low profile; ability to pass through introducer sheaths; ability to negotiate tortuous vasculature, smoothly and atraumatically; protection of constrained devices; and ability to accurately position and deploy the device.

Traditionally, stents or stent-grafts have been designed either to plastically deform (e.g., "balloon expandable" stents) or to elastically recover (e.g., "self expandable" stents) from a collapsed, introduced diameter to an expanded, functional diameter. Stents that are typically designed to elastically recover are manufactured at their functional diameter, and then radially compressed to be mounted on a delivery catheter. These devices must often be constrained in this compressed state for a prolonged period of time. Additionally, there must be a mechanism to release this restraint remotely and allow the device to elastically recover to its functional diameter when properly positioned.

A number of techniques are practiced to constrain elastically compressed stents and allow the restraint to be removed from a remote site. One technique involves placing the stent in the annular space between two concentric catheter tubes. The inner tube facilitates passage of a guide wire through its inner diameter, and the stent or stent graft is elastically compressed on its outer diameter. The outer catheter tube or sheath then is placed over the compressed device, effectively capturing the compressed device. When it is desired to have the stent recover to its functional diameter, the other tube is pulled back relative to the inner tube, and the device elastically recovers. This deployment can be activated remotely (for example, at the hub end of a catheter) by longitudinally displacing the tubes relative to each other.

A variance of this concept is to have another concentric tube, located concentrically between the outside and inside tube. By moving this third tube relative to the other tubes, the elastically constrained device can be pushed from the catheter, allowing it to elastically recover to its functional diameter. The inner tube, through whose lumen a guide wire passes, could be removed for a further variation in this design. In the modified design, the guide wire would pass in the lumen of the pushing tube and through an unprotected lumen of the collapsed endoprosthesis.

Another possible technique that can be employed uses a suture that is stitched to the stent or stent graft in its collapsed, elastically constrained diameter. In one embodiment of this technique, a "chain" stitch of removable suture is made through the metal struts of a collapsed stent. One end of the stitch can then be pulled, from a remote location, releasing the stent to elastically recover.

Another technique involves encasing the collapsed endoprosthesis in a thin-walled wall casing that is held in a tubular configuration by a chain stitch of removable thread (e.g., a suture) applied to a longitudinal seam. When the stitch is removed, the seam is opened as the stent elastically recovers to its operational diameter. This release mechanism leaves the thin wall casing captured between the device and the tube in which it was deployed.

The devices employed for constraining elastically deformed stent or stent grafts and remotely deploying them have a number of problems. One desired feature of an undeployed stent is that it be flexible on the catheter. This allows the catheter to be easily manipulated through the path it must negotiate from its entry site to the site where the device is to be deployed. When concentric catheter tubes are employed, this construction usually creates large cross-sectional dimensions and is stiff, making navigation through tortuous vascular segments difficult. Also, the need to manipulate multiple tubular components can make accurate placement of the stent or stent graft difficult. Another typical problem is that large forces are often required to retract the sheath or to push out the stent.

There are many other desirable features for a stent or stent-graft delivery system. For instance, it is very beneficial for the exterior surfaces of the collapsed endoprosthesis to be smooth and, therefore, more atraumatic to host vasculature. Additionally, it is desirable for the system to work with any elastically recoverable stent. Further, it is desirable for the delivery system to have sufficient strength to radially constrain the device during its normal shelf life without "creep" dilatation.

For delivery systems that include a removable suture through the stent, the systems effectiveness in restraining the device depends greatly on the endoprosthesis design. The struts of the endoprosthesis can be exposed in its collapsed diameter, and this can potentially cause trauma during navigation to the treatment site. Additionally, exposed struts may also cause difficulties with deployment (for instance, entanglement of deployment suture or struts).

A disadvantage of the thin-walled casing devices is that the encasing sleeve is left in-vivo after the endoprosthesis has been deployed, which may inhibit healing or endothelialization of the luminal surface and cause flow stream disruption. Also, these devices may add significant profile to the catheter, and are detrimental to the catheter's flexibility. Finally, another problem with current delivery systems that use single removable threads to facilitate deployment of the endoprosthesis is that these cords must be designed to be strong in tension so that they do not break during the removal process. This requirement usually dictates that larger diameter threads must be used than are needed to hold the endoprosthesis in its elastically collapsed configuration to avoid tensile failure during deployment.

Some of these deficiencies are addressed in U.S. Pat. No. 4,878,906 to Lindemann et al. and U.S. Pat. No. 5,405,378 to Strecker. Both of these patents employ a one or more contiguous removable thread around an expandable prosthetic that can be remotely removed through a catheter tube or the like. While these methods of prosthetic deployment may offer some improvement over other deployment methods, the open-structure nature of these constraints are believed to provide only limited and localized resistance to the force exerted by a self-expanding prosthesis. Other possible problems with these devices include: uneven distribution of constraining force radially and along the length of the prosthesis; high stresses on a single deployment suture that may lead to breakage risks during deployment; inadequate coverage of the outside of the prosthesis—possibly leaving a rough exposed surface; and undesirable back-and-forth movement of the constraining/deployment filament over the exterior surface of the device during deployment, which may lead to potential entanglement or embolism formation. This is sometimes referred to as a "windshield wiper" effect.

Accordingly, it is a primary purpose of the present invention to provide an improved apparatus and method of deploying a self-expanding device, such as an endoluminal stent or the like.

It is a further purpose of the present invention to provide an apparatus and method for deploying a self-expanding device that provides excellent constraint and coverage of the device in a non-deployed state and ease of deployment of the device once it has been properly positioned.

These and other purposes of the present invention will become evident from review of the following specification.

SUMMARY OF THE INVENTION

The present invention is an improved cover for a self-expanding device that is both effective at maintaining the self-expanding device in a constrained initial orientation and is easily removable during the deployment procedure. In its preferred form, the device of the present invention comprises a warp knit (also known as a "knit-braid") of two or more interlocking strands of thread that forms a relatively tight cover (or "encasing") around the self-expanding device. Each of the threads covers only a portion of the outer circumference of a radially compressed device. By imparting a break in one filament of the knit-braid at one end of the cover, the cover can be removed in its entirety through simple application of tension in any direction to a multi-filament "rip cord." The rip cord is contiguous with the cover, which allows the cover to be removed in its entirety when subjected to tension while the self-expanding device expands in place. This construction has many advantages over previous devices, including allowing removal of the cover along a single vector without the deployment rip cord undergoing the windshield-wiper effect.

The device of the present invention resists high internal pressures with minimal radial growth, although very low forces are required to remove the cover. To remove the cover, the high-strength knitted multi-filament rip-cord can be pulled from any direction. This knitted rip cord is integral to the cover, and is comprised of two or more fibers. Consequently, only thin walled covers (and consequently small diameter rip-cords) are required to constrain the device. This cover can be removed in a controlled fashion and controlled rate. Additionally, the knit-braid construction allows radially-constraining forces to be uniformly distributed over the surface of the self-expanding device while retaining excellent flexibility.

The cover of the present invention can provide a wide degree of coverage, varying from greater than 100% to less than 10%. Additionally, the cover has a relatively smooth surface texture, and is completely removable. The cover can be made from a thin film or fiber, with the preferred material being an expanded polytetrafluoroethylene ("ePTFE"). Also, the cover of the present invention can be used to enhance the smoothness of tapers and transition regions in the pre-deployed device and associated delivery system, such as where the device is attached to a catheter.

The cover of the present invention can also be sequentially formed over different sections of a catheter. For example, the warp knit can be formed to allow the ends of a stent to be deployed stage-wise before its center, an outer covering can be released before the inner covering, etc. These performance characteristics can be achieved using a single rip-cord or multiple rip-cords. The "density" of the braid can also be varied to provide different deployment functions. This feature can enable an appendage or a guide wire to exit from the side of the braid.

Additional advantages of the present invention are that it is easy to manufacture, can be easily automated, and, during manufacturing, the knitting process supplies radial compressive forces to the self-expanding device, potentially further decreasing its profile. The cover of the present invention also allows for adjustment of the flexibility of the entire delivery system, by using the presence, absence, and/or varying degrees of coverage of the cover to modify portions of the delivery system to be any where between quite stiff to very flexible. The ability to adjust the flexibility of the system allows the pre-deployed device to be tailored to be pushable and/or track-able.

This technology is believed to be particularly useful as a cover around self-expanding endoluminal devices, such as stents, grafts, stent-graft combinations, and the like used in blood vessels, and other body passageways (referred to collectively herein as "stents and grafts"). Additionally, the device has many other potential medical applications. For example, the cover of the present invention can be used with balloon dilatation catheters and/or balloon expandable stents and grafts to create variable length and/or diameter balloons. This technique can also be used to control the direction of deployment of the balloon or implantable device. Other self or mechanically expanding devices, such as embolic coils or vena cava filters, can also be delivered using the disclosed delivery system of the present invention. The system of the present invention can likewise be used to deliver multiple devices on one catheter. Further, the present invention may be employed to allow for removable guide wire lumens to be manufactured on catheters, either by having the cover define a guide wire lumen or having the cover join multiple catheter tubes together. The cover can also be used to bundle multiple guide wires together, increasing their pushability while they are being delivered but allowing them to be separated as appropriate within a patient. Also, the cover can be used on an infusion or suction catheter to vary the fluid resistance into or out of the catheter.

Non-medical applications also exist for this technology. The cover of the present invention can be used as a filter that is removable from a remote site. This would be advantageous for hazardous environments. The inventive cover may also be used for insulating wires, allowing for an easy way to strip the insulation from the wires. The cover can be used to allow for compressed packages to be released with the pull of a single rip-cord, for potential use in marine life saving or parachute-style devices. The cover may also be used to encase highly pressurized packages that can be released to their lower pressurized, higher volume state. This could be used to rapidly pre-inflate devices such as bicycle tires. The cover may also be used for packaging of non-full density items, such as insulation or sponges or bundling supplies (e.g., kits) in a secure fashion requiring rapid use and minimal packaging waste (e.g., for emergency, EMT, military, or similar applications).

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved cover for use on a constrained device, and particularly on a self-expanding device. As will become evident from review of the following description, the present invention can be used in a variety of medical and non-medical applications. Although not limited to such procedures, the present invention is particularly useful for use as a cover over endoluminal implantable devices, such as stents and grafts, catheters, endoluminal balloons, and the like.

The terms "cover," "encasing," "casing," and "sheath" as used herein are intended to encompass any structure that contains another device (or multiple devices) or any part thereof, such as a implantable prosthetic, a guide wire, a guide wire lumen, a balloon catheter, et cetera. The terms include, without limitation, structures that provide an outer sheath to such devices as well as other structures that might be further encased in other layers of materials, other devices, and/or multiple layers of covers of the present invention.

Figure 1:
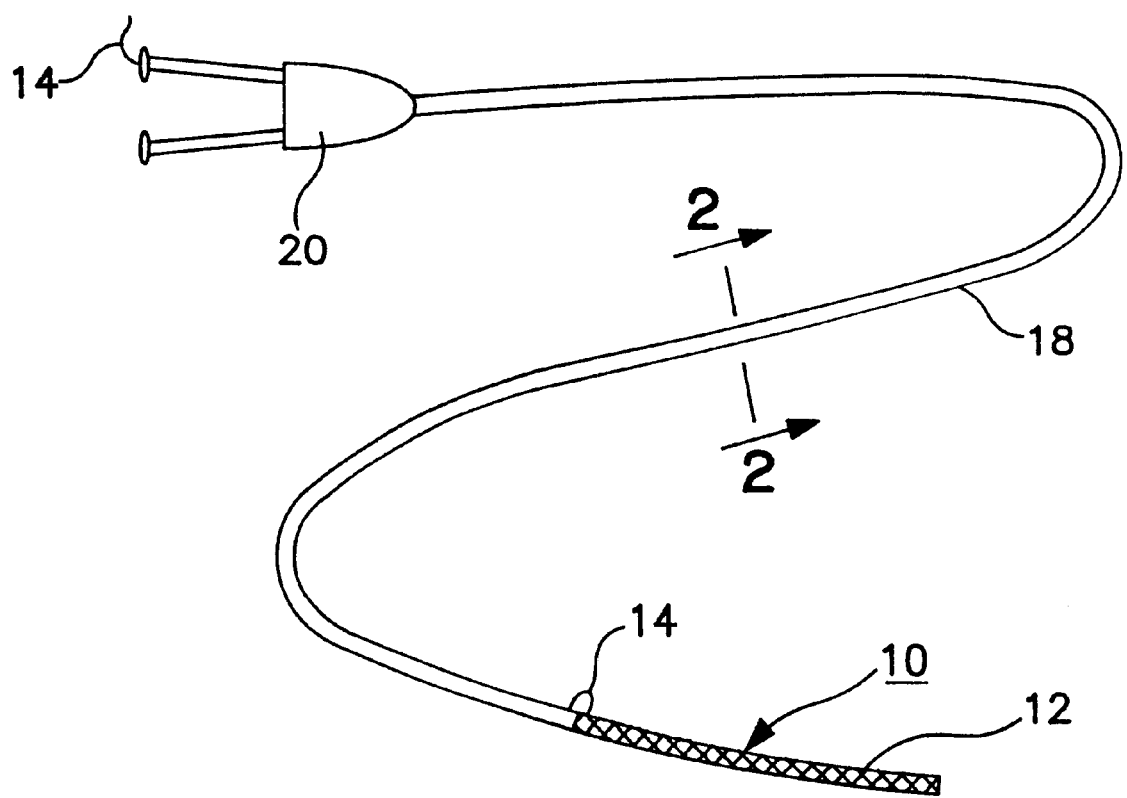
FIG. 1 is a top plan view of a dual lumen catheter with a cover of the present invention installed on a distal end of the device and a rip-cord of the present inventions routed through one of the lumens.
Figure 2:
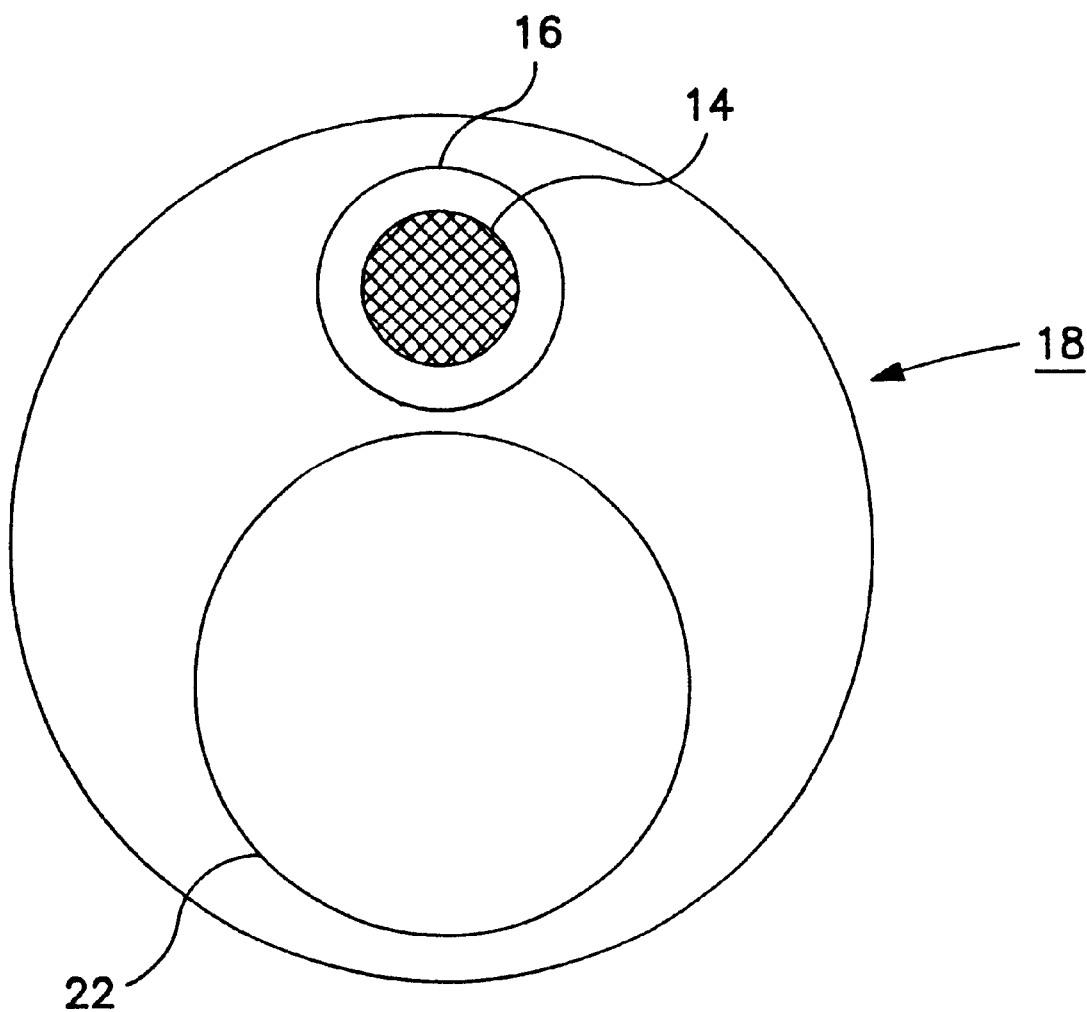
FIG. 2 is a cross section view along line 2—2 of FIG. 1.

One use of the present invention is illustrated in FIGS. 1 and 2. The present invention comprises a knitted cover 10 that is used to encase another device, such as an elastically deformable stent 12. A multi-filament rip cord 14 is formed at one end of the cover 10 and should be of sufficient length to allow the cover to be unfurled at a distance from the cover 10. As can be seen, the rip cord 14 actually comprises a multiple-strand extension of the knitted cover itself. In the embodiment illustrated, the rip cord is mounted within a first lumen 16 of a double lumen catheter 18 and exits through a Y connector 20. A second lumen 22 is provided for manipulating the catheter 18 and stent 12 into position along a guide wire (not shown).

Figure 3:
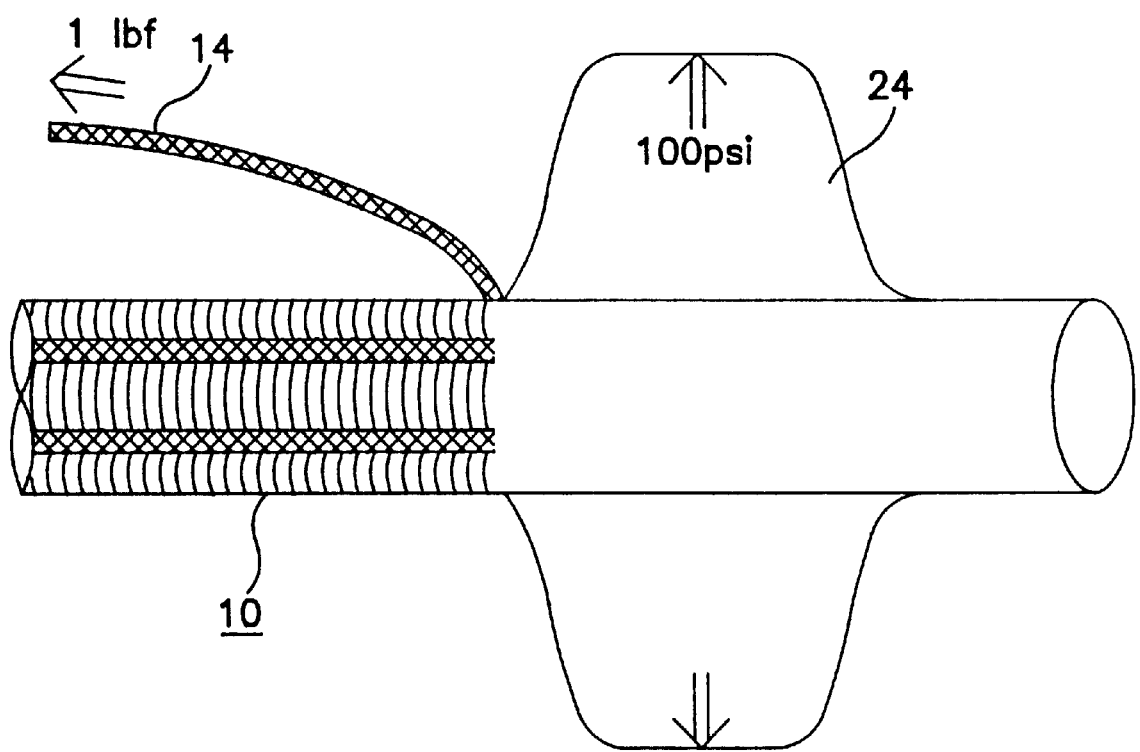
FIG. 3 is a side elevation view of a cover of the present invention shown partially removed from a balloon dilatation catheter.

The cover of the present invention has unique properties derived from its particular knitted structure. As is explained in greater detail below, by forming a knitted cover using a particular knitted pattern known as "warp knit" or a "knit-braid" and then specifically preparing the cover for removal, the entire cover of the present invention can be removed by simply pulling on the rip cord 14 device. As is shown in FIG. 3, the cover 10 can be used to cover, for example, a balloon on a balloon dilatation catheter 24 or a self-expanding tubular device and then removed by pulling on the rip cord 14. The knit-braid cover 10 will then unravel to allow the balloon 24 or a self-expanding device to enlarge along its length concurrently with the removal of the cover, as shown.

Figure 4:
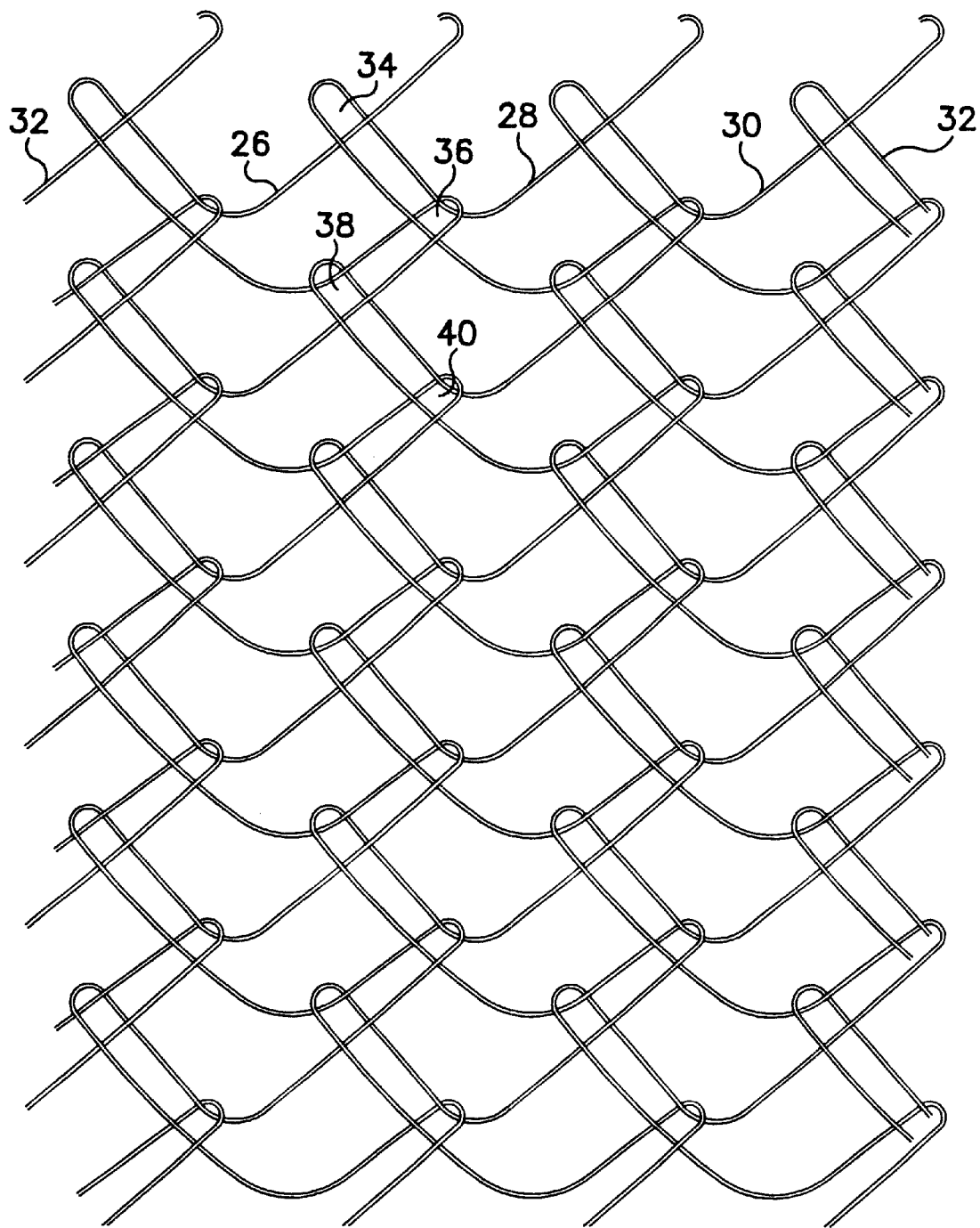
FIG. 4 is an enlarged plan view of a warp knit pattern used to form the cover of the present invention, the knit-braid employing four different strands, each of which covers only a portion of the circumference of the self-expanding device.
Figure 5A:
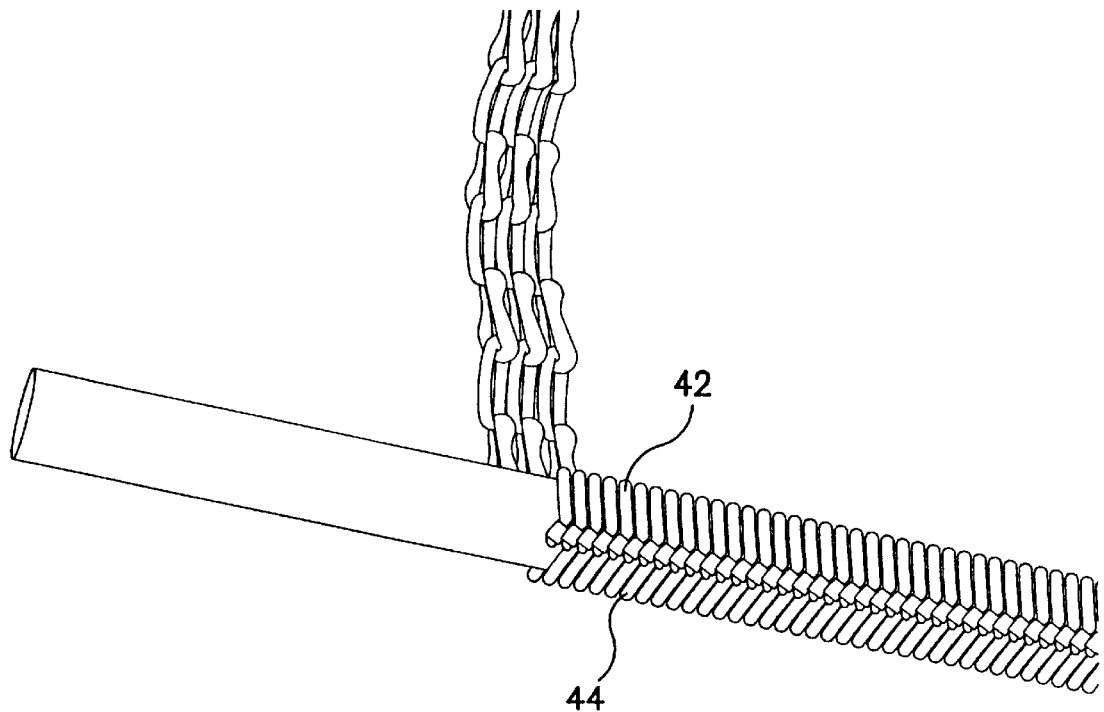
FIGS. 5A through 5D are side elevation view of the cover of the present invention being removed from a tubular substrate, the four figures illustrating the process of removal of the interlocking strands of the cover.
Figure 5B:
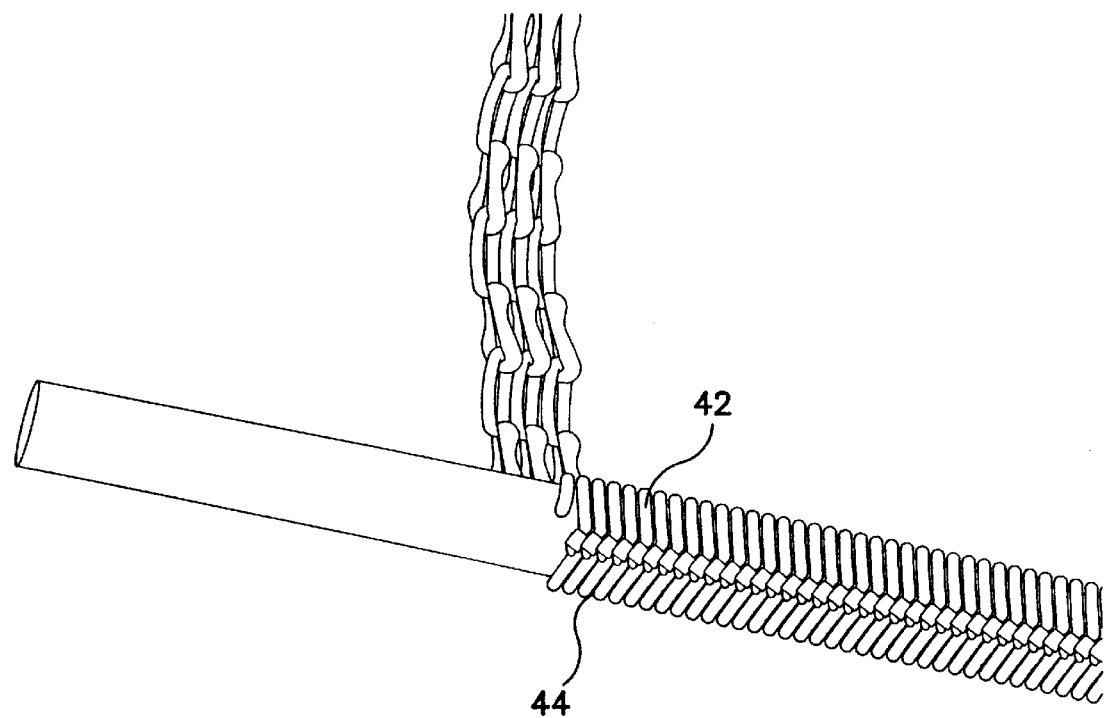
Figure 5C:
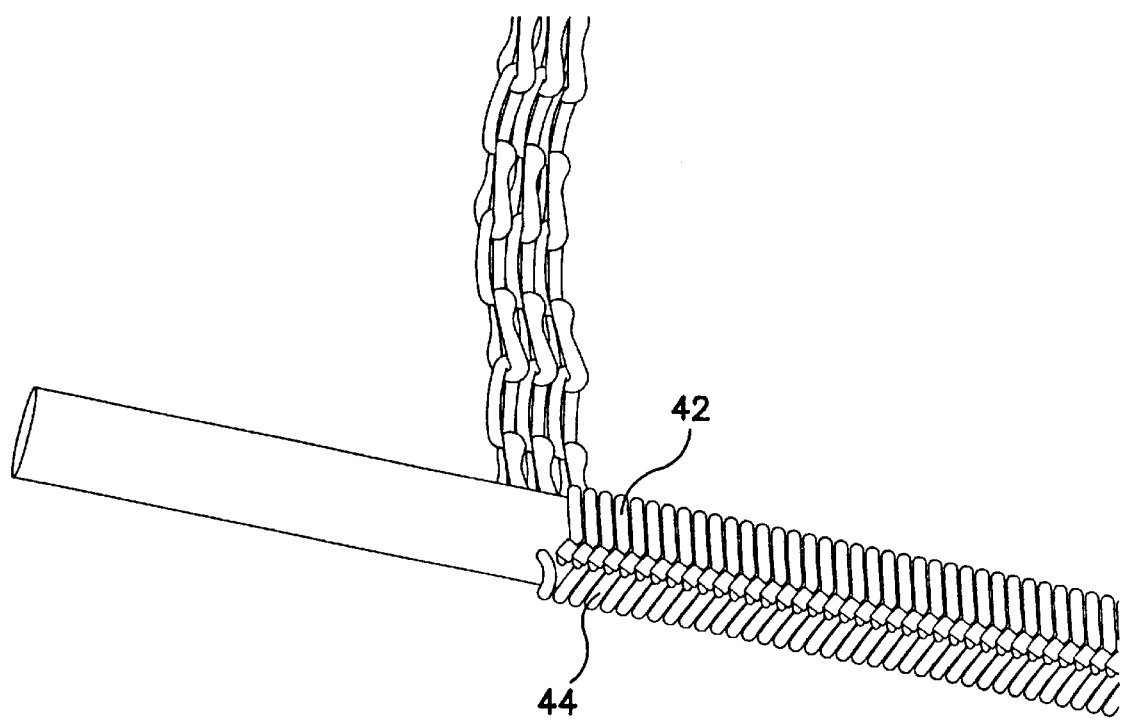
Figure 5D:
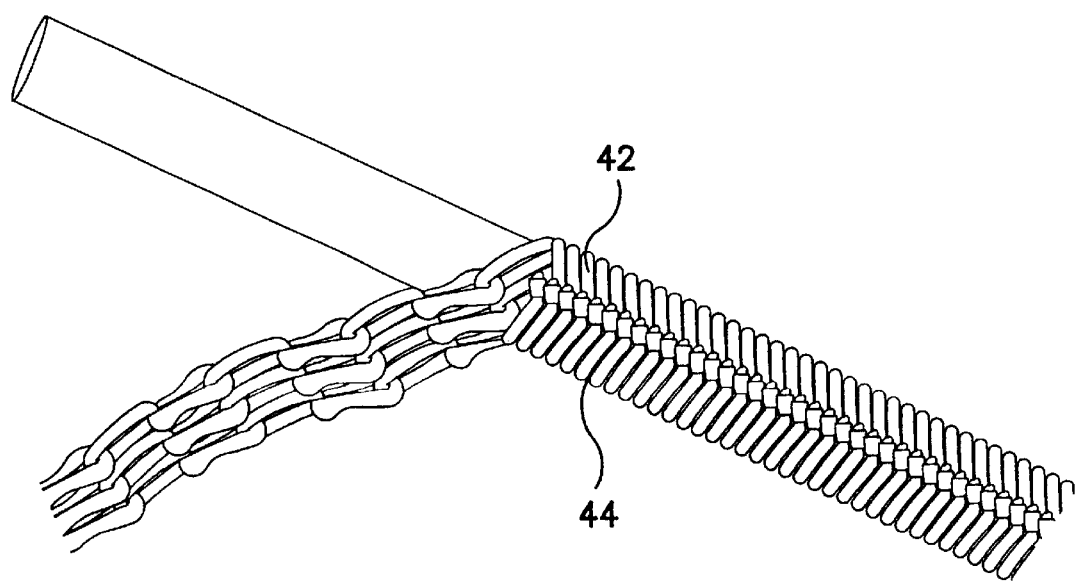

FIG. 4 illustrates one preferred embodiment of a warp knit cover 10 of the present invention. The cover 10 illustrated comprises four different strands of fiber 26, 28, 30, and 32 that are interlocked together. Starting with a minimum of two independent filaments, as many strands as desired and appropriate can be combined in this manner, with a tubular structure being formed by simply interlocking the final strand with the first. Specifically, this structure works in the following manner. The first strand 26 loops around the second strand 28 and the fourth strand 32. In turn, the second strand 28 loops around both the first strand 26 and the third strand 30. Similarly, the third stand loops around the second strand 28 and the fourth strand 32. Finally, the fourth strand 32 loops around the third strand 30 and the first strand 26 to form a tube.

This interlocking structure will completely unravel as a coherent interwoven multi-filament rip cord by simply separating one of the strands from the rest at one end. For instance, with tension applied to the top side of the knit, if the first strand 26 releases at connection point 34 (such as by cutting or detaching the strand at that point), then the second strand 28 will release from the first strand 26 at connection point 36. Subsequently, the first strand 26 will release from the second strand 28 at connection point 38, and the second strand 28 will release from the first strand 26 at connection point 40. This process will continue along the entire length of the device until the entire cover disengages as one long, continuous, interwoven rip cord.

This process can be further appreciated through review of FIGS. 5A through 5D, which illustrate the process of disengagement of each of the loops of fiber of the present invention in a four fiber 42, 44 tubular construction.

There are numerous advantages to making a cover in this manner. First, the cover has proven to be quite strong with respect to radial dilation forces. The ability to use as many strands as is desired, with as tight a knit pattern as is desired, allows the cover to provide very complete containment of the self-expanding device and uniform distribution of constraining forces over the surface of the self-expanding device. The term "uniform distribution" is intended to mean that essentially the same constraining force is applied around the circumference of the device (i.e., so the device does not bulge on one side) and/or along the longitudinal length of the device (i.e., so the device has a consistent profile along the length of the device). Despite the security of containment, the cover will very rapidly disengage from the self-expanding device by simply pulling on the rip cord. By way of example, it has been demonstrated that the cover of the present invention can contain a device exerting over 100 psi expansion force. However, once expansion is appropriate, the cover can be completely and easily removed from the device simply by exerting as little as 1 lb. tensile force along the rip cord.

Figure 6:
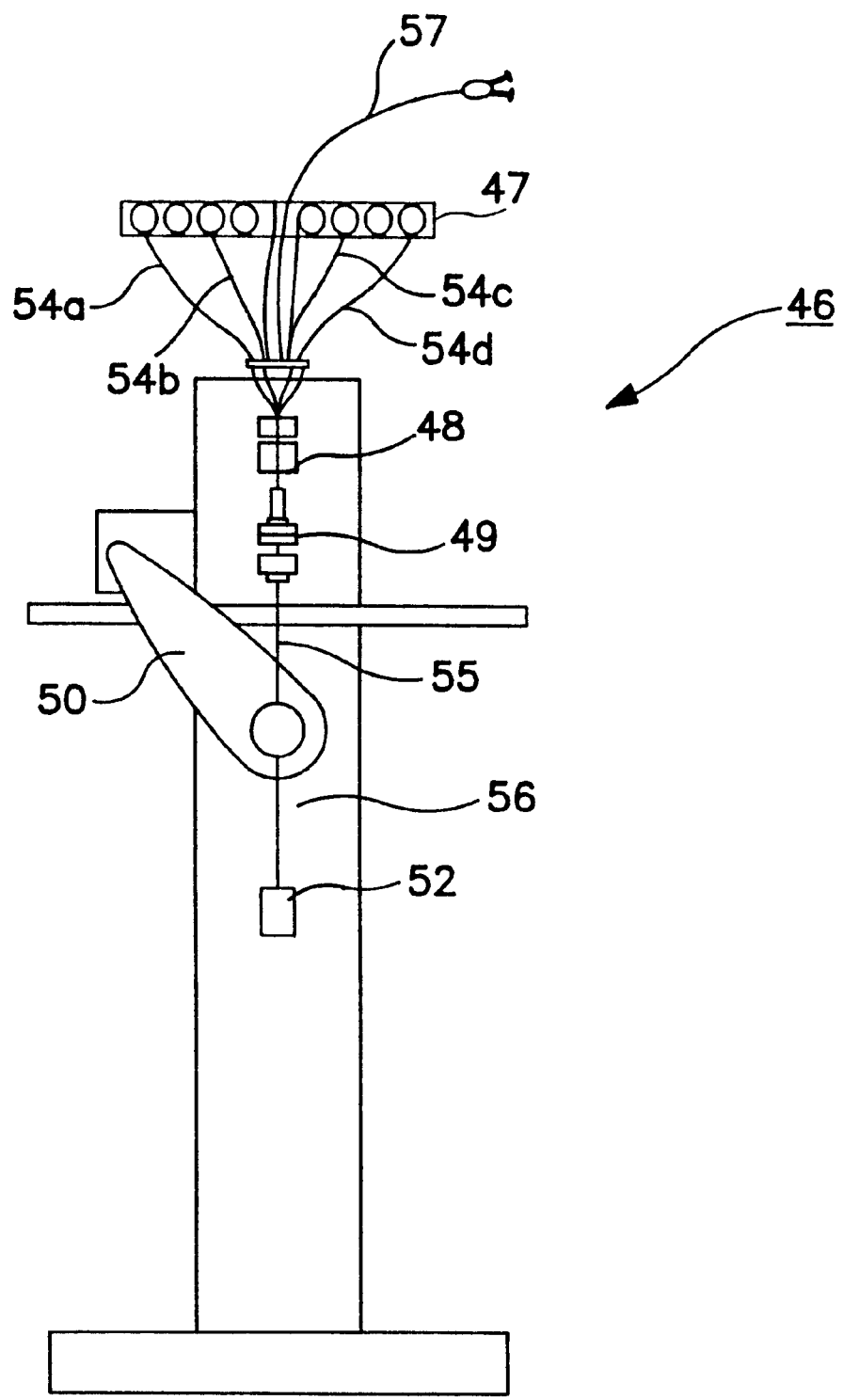
FIG. 6 is a side elevation view of one embodiment of apparatus used to create a warp knit of the cover of the present invention.

Another advantage of the cover of the present invention is that it can be readily formed in-place around a self-expanding device. For instance, FIG. 6 illustrates a warp knitting (or knit braiding) machine 46, Model No. 2NBA/Z-TB, available from Lamb Knitting Machine Corporation of Chicopee, Mass. The device illustrated comprises a thread pinch tensioning device 47, a thread position shuttle 48, a knitting head 49, a take down unit 50, and a weight 52. The knitting head 49 employed is an eight needle head with every other needle removed (for a total of four needles) and a core diameter of ⅜ inch (9.5 mm). In use, filaments 54a, 54b, 54c, 54d are fed through the tension system and the filaments guides 47 into the shuttle 48 and the knitting head 49 and are attached to weight 52. The knit braiding machine will automatically intertwine the filaments 54 into a joined warp knitted tube 55. The knot 56 serves to hold the knit-braided tube 55 together. The weight 52 applies tension to the filaments 54 to assist in feeding the filaments through the system. The take down unit 50 is not required in this process and should be disabled.

This device 46 is readily adapted to create a cover of the present invention. In this regard, a device to be wrapped, such as an endovascular prosthesis (not shown) on the end of a catheter 57, is fed down through the thread position shuttle 48 and the knitting head 49. The knitter will apply the warp knit tube 55 around the prosthesis to form a cover of the present invention.

The nature of the knit-braid created by this machine 46 allows the ends of the final tube to be pulled longitudinally to apply greater compressive force to the wrapped device.

Figure 17:
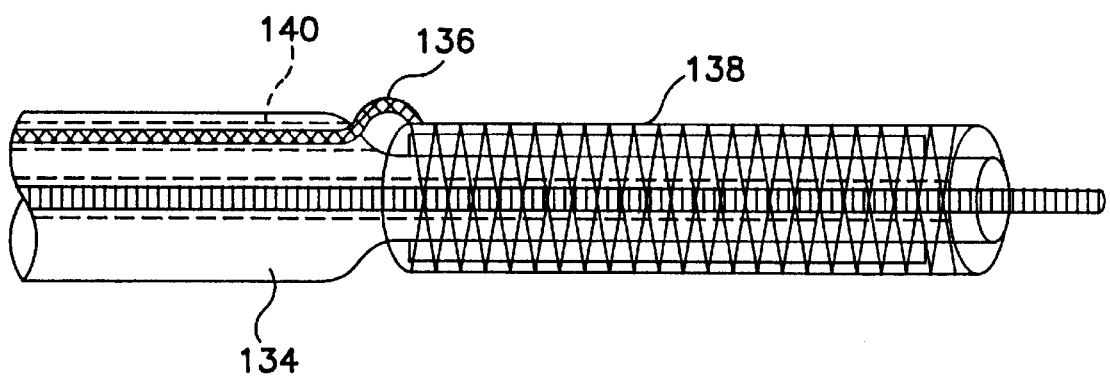
FIG. 17 is a side elevation view of a further embodiment of a cover of the present invention, this cover comprising a rip cord threaded into one lumen of a dual lumen catheter.

Following the wrapping process, the cover is finished over the wrapped device as follows. The knit is unfurled through a length of catheter up to the location on the catheter where the endoprosthesis is compressed. This unfurling is started by breaking one of the fibers on the closed end of the knit. This unfurled length of knitted thread then can be routed to the hub of the catheter to serve as the rip cord to deploy the stent. Preferably, this rip cord is fed through one lumen of the catheter as depicted in FIG. 17.

It has been demonstrated that by employing a knit-braid apparatus of this form a tight wrap can be applied around a self-expanding article. In fact, the mere act of forming the cover has been demonstrated to apply compressive forces to further assist in constraining the self-expanding device.

One particular important advantage of the present invention is the cover's ability to unfurl along a "single vector". The warp knit pattern of the present invention will separate along essentially a straight line (which may be purely linear or, where desired, along a spiral or any other pattern along the device). Similarly, the rip cord pulls away from the constrained device along an essentially straight line. The term "single vector" as used in this regard refers to the cover separating or removing from the device in an essentially straight line when tension is applied to the rip cord without the extreme "windshield wiper" motion of some current thread-wrapped devices exhibit. For a two-thread symmetrically applied cover, this means that separation of threads will occur over no more than about 180 degrees of the circumference of the covered device; for a symmetrical three-thread cover, separation will occur over no more than about 120 degrees of the circumference of the covered device; for a symmetrical four-thread cover, separation will occur over no more than about 90 degrees of the circumference of the covered device; for a symmetrical five-thread cover, separation will occur over no more than about 75 degrees of the circumference of the covered device; for a symmetrical six-thread cover, separation will occur over no more than about 60 degrees of the circumference of the covered device; and so on.

When cover separates in this manner, the rip cord will remove all of the fibers from the device in an essentially straight line or "single vector". The elimination of the windshield wiper effect is believed to significantly decrease the risk of entanglement during cover removal. Additionally, single vector removal also imparts significantly less trauma to the host vessel during removal, reducing the risk of embolization and other complications.

It should be appreciated that the threads of the present invention need not be symmetrically applied. For example, different weights of thread may be used. Additionally or alternatively, each of the sets of threads may be applied to cover a different proportion of the circumference of the device, allowing separation to occur over a greater or lesser proportion of the circumference.

Another important aspect of the present invention is the fact that the cover separates as a multi-filament interlocking structure. This separation mechanism provides significant increased overall strength to the rip-cord during removal. This vastly improves the design options for creating sheaths, such as allowing thinner material to be used with less risk of breakage. Additionally, the interlocking structure is more readily removed, with less risk of accidental separation during the removal process.

Another method of forming a cover of the present invention involves using a structure external to the warp knit to allow a stent to be drawn into the warp knit lumen. For example, a warp knit (four threads, ⅜" root diameter) can be knitted on a 304 stainless steel one foot long mandrel that has an outside diameter slightly larger than the diameter of the compressed device. Then the warp knit/mandrel is hand wrapped with approximately 15 layers of pipe thread tape (e.g., Poly-Temp Teflon® Tape, available from Anti-Seize Technology, Franklin Park, Ill.) and this assembly is placed in an air convection oven at 370° C. for 5 minutes. After cooling this assembly, the warp knit/external pipe thread tape support is stripped from the mandrel using a concentric tube that snugly fits the mandrel and pushing the warp knit/tape support off of the mandrel using this concentric tube. The self-expanding stent can then be drawn through a funnel directly into this externally supported warp knit. The pipe thread tape is then removed by carefully removing each layer of this tape. The resulting structure is a collapsed diameter stent in a warp knit cover. This cover can be removed by pulling two or three of the four threads of the knit from the end of the knit that was last knitted. The self-expanding stent is then self deployed with the cover removed.

The cover of the present invention can be made in a wide variety of constructions, using a wide variety of possible materials. For instance, the knit structure can employ anywhere from 2 to 16 or more threads, with 3 to 8 threads preferred and 4 to 6 threads most preferred. The density of the knit may range from 2 to 80 knits per centimeter, with 10 to 50 preferred. The knit may be constructed with a complete coverage of the covered device (that is, 100% of the surface area of the device covered) or more (such as by overlapping the threads to form multiple layers) to as little as 1 to 5% coverage of the surface area. For most applications, the preferred coverage will be about 10 to 100%.

Percentage coverage in the context of the present invention may be determined by approximating the amount of outside surface area of the covered device covered by the warp-knitted cover of the present invention relative to the amount of outside surface area that is left exposed (that is, the area left without threads of the cover extending over it).

Other structural modifications can also be incorporated in the cover of the present invention. For example, it is possible to form at least two of the stitches spaced circumferentially close to each other, and this may be accomplished by having higher pinch tension on at least one of the input strands employed during the knitting process as compared to the other input strands. Still another structural modification is to use input strands with different characteristics, such as employing one or more strands with particular desirable properties (e.g., making a strand radio-opaque to aid in fluoroscopic visualization, or using strands of different deniers, texture, or other properties) Still another modification of the present invention is to employ a cover that extends beyond the ends of a covered device to cover an adjacent structure, such as a catheter. By forming a cover in this manner, a gradual transition in profile can be established from a catheter to a covered device. This construction is shown, for example, in FIGS. 12, and 23A.

The materials used to make the cover of the present invention are likewise open to modification and customization for given applications. For most uses discussed herein threads or other fibers are used to form the cover. Suitable threads include: polytetrafluoroethylene (PTFE); expanded PTFE; silk; thermoplastic threads such as polypropylene; polyamide (nylon); various plastic or metal materials (e.g., stainless steel or nickel-titanium (nitinol) alloy); and bioresorbable materials, such as PLA or PGA. The threads may be used within a wide range of deniers, such as 25 to 2500 (grams/9000 meters). Particularly preferred for use in covering implantable medical devices are polytetrafluoroethylene (PTFE) threads, and especially expanded PTFE threads, such as threads available from W. L. Gore & Associates, Inc., Elkton, Md., under the trademark RASTEX® or sutures available from W. L. Gore & Associates, Inc., Flagstaff, Ariz., under the trademark GORE-TEX®.

By way of example, to cover a 10 mm diameter WALLSTENT® stent (available from Schneider, Inc., Minneapolis, Minn.), a four thread cover of CV-8 GORE-TEX® suture having a denier of about 150 and a percentage coverage of about 25% is believed preferred.

It should be appreciated that other materials may also be suitably employed with the present invention. For example, in place of one or more fibers a film or other structure may be substituted to impart particular performance characteristics. Examples of other suitable materials include tapes, single filament threads, multi-filament threads, beading, etc.

As to particular applications for the cover of the present invention, FIGS. 7 through 23 provide examples of devices that can benefit from use with a cover or covers of the present invention.

Figure 7:
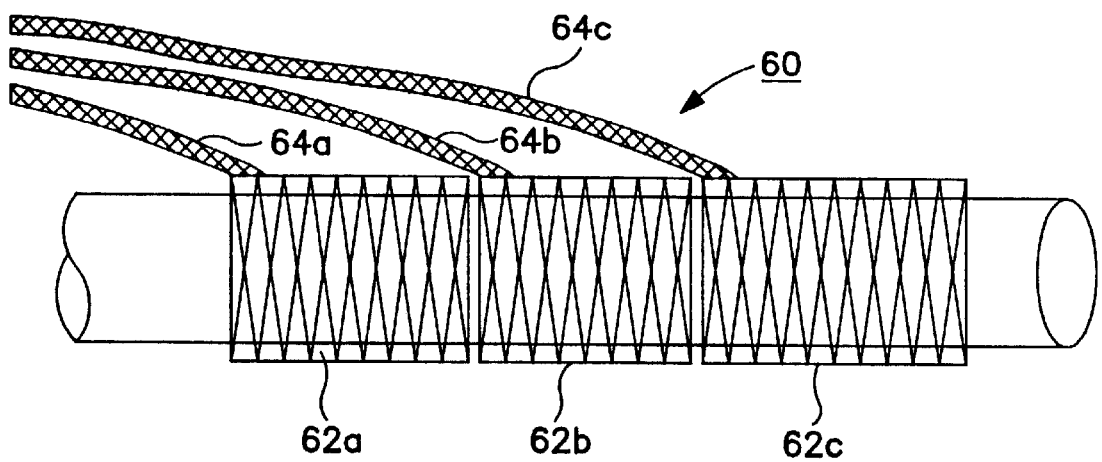
FIG. 7 is a side elevation view of a further embodiment of a cover of the present invention, this cover comprising multiple cover segments each controlled by separate rip cords.

FIG. 7 is a further embodiment of a cover 60 of the present invention, this cover comprising multiple cover segments 62a, 62b, 62c, each controlled by separate rip cords 64a, 64b, 64c, respectively. This configuration allows each of the cover segments to be separately removed from a covered device 60 in whatever order is most desired. By covering a self-expanding stent device in this manner, a surgeon can opt to selectively expand the distal, middle, or proximal ends of the device as best suits a given procedure.

Figure 8:
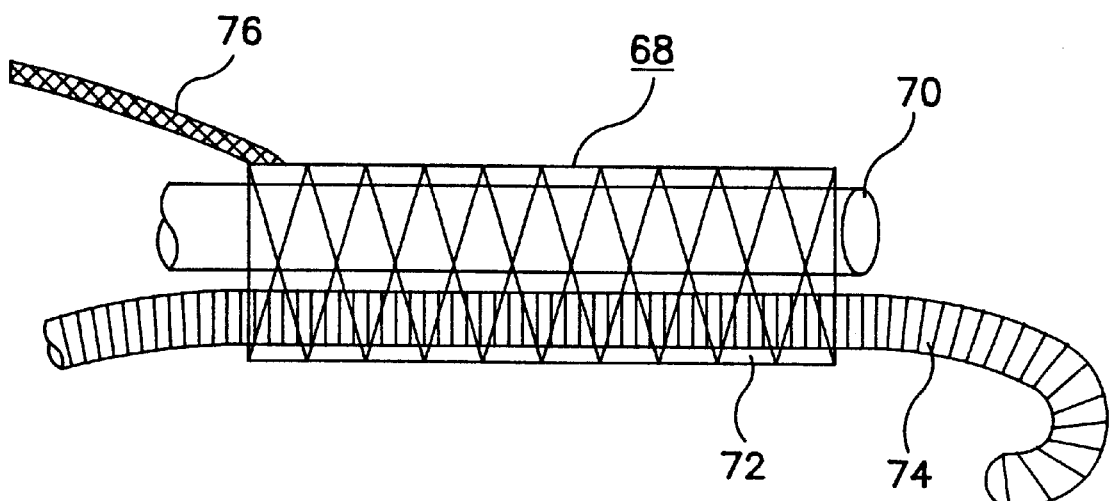
FIG. 8 is a side elevation view of another embodiment of a cover of the present invention, this cover including a catheter and a removable guide wire lumen.

FIG. 8 is another embodiment of a cover 68 of the present invention wherein the cover is used to contain multiple devices. In this instance, cover 68 contains a catheter 70 and a removable guide wire lumen 72. This construction allows for a guide wire lumen to be temporarily joined together for ease in passage through a blood vessel and then separated by removing the cover using the rip cord 76 once they have been properly positioned. The guidewire then remain in-situ allowing for an additional catheter device to be positioned.

Figure 9A:
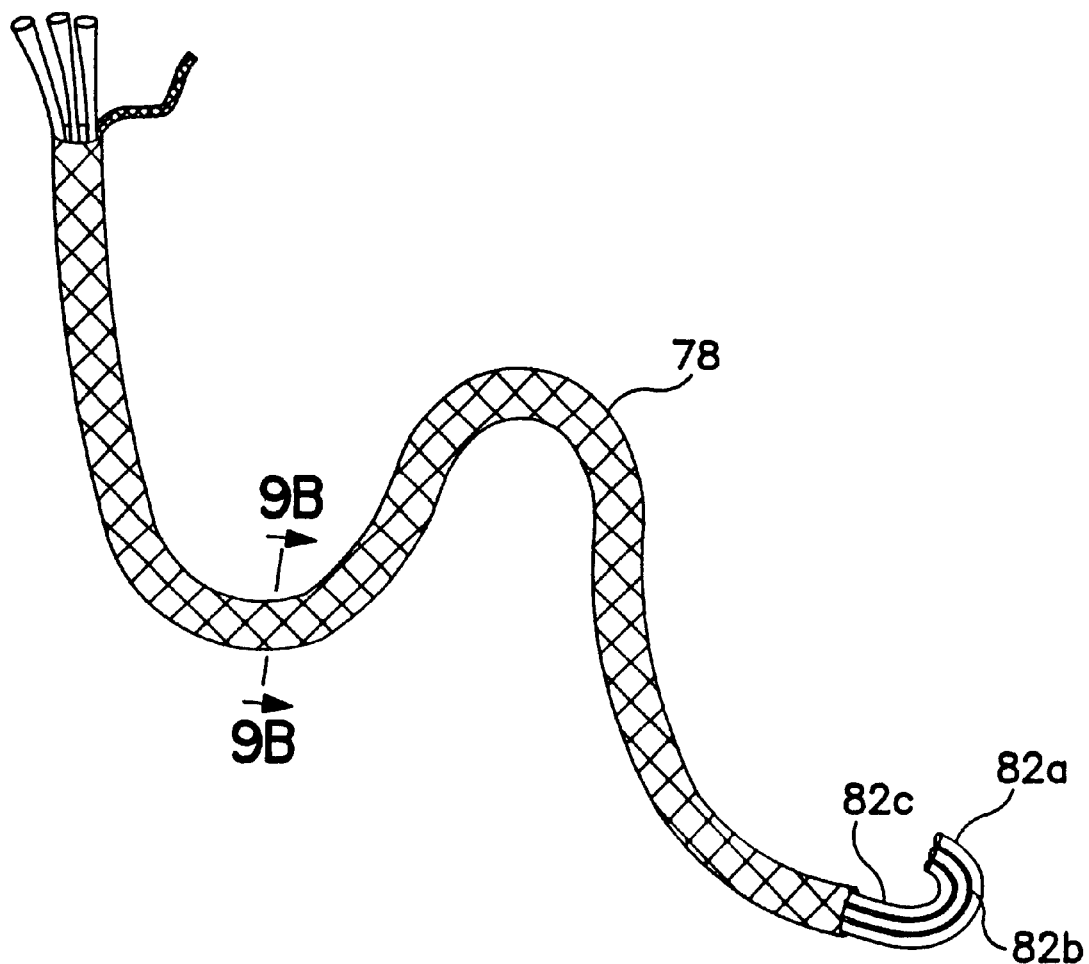
FIG. 9A is a side elevation view of a still another embodiment of a cover of the present invention, this cover comprising a multiple guide wire casing.
Figure 9B:
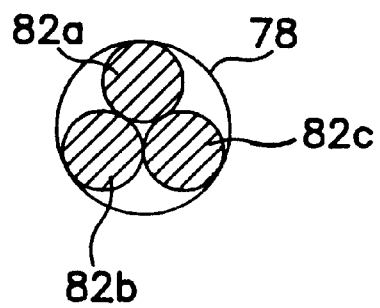
FIG. 9B is a cross-section view along line 9B—9B of FIG. 9A.

FIGS. 9A and 9B illustrate still another embodiment of a cover of the present invention. In this instance, the cover 78 contains multiple guide wires 82a, 82b, and 82c. Again, this construction provides means to retain multiple devices together for insertion into a body and then separate them from each other once in place.

Figure 10:
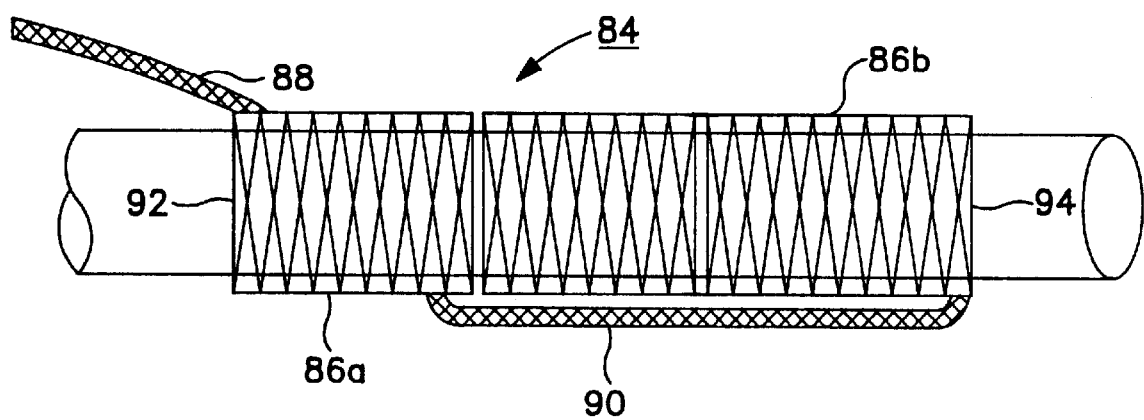
FIG. 10 is a side elevation view of yet another embodiment of a cover of the present invention, this cover comprising multiple cover segments each controlled by a single rip cord.

FIG. 10 illustrates a cover 84 comprising multiple cover segments 86a, 86b. A master rip cord 88 is provided attached to segment 86a, and a secondary rip cord 90 is provided attaching segment 86b to segment 86a. Constructed in this manner, tension on proximal end 92 of the cover via master rip cord 88 will first release segment 86a. Once segment 86a has been fully released, the secondary rip cord 90 will begin releasing segment 86b from the distal end 94 of the cover. In this manner, a non-end-to-end (or "non-linear") cover release can be effectuated with tension on a single rip cord 88.

Figure 11:
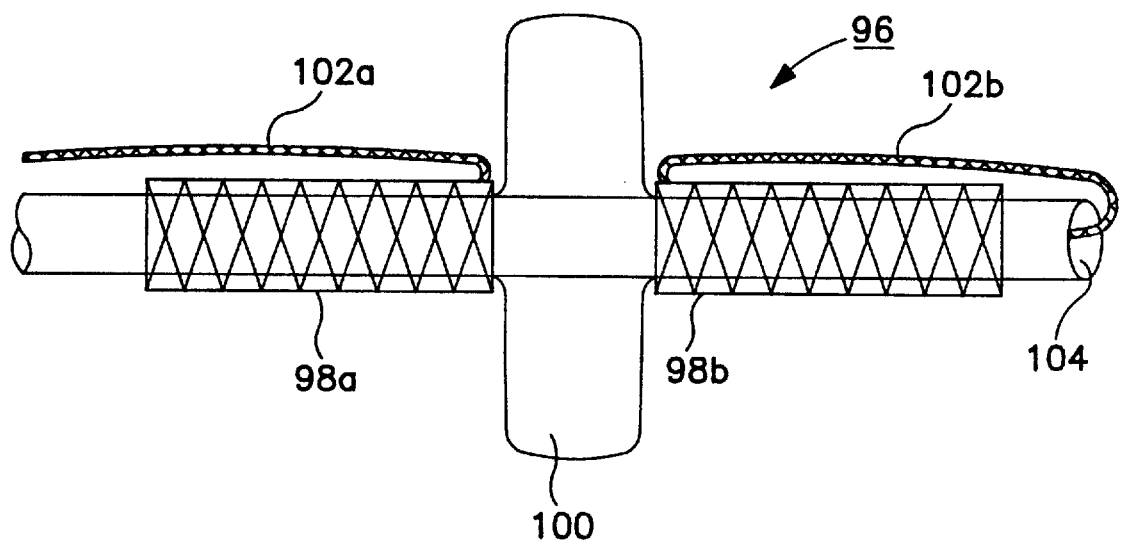
FIG. 11 is a side elevation view of a further embodiment of a cover of the present invention, this cover comprising two separate segments, each separating from a covered balloon dilatation catheter from a center position, allowing the balloon dilatation device to lengthen axially from its center.

The embodiment of FIG. 11 is a cover 96 having two separate segments 98a, 98b covering a balloon 100 (with each segment shown partially withdrawn and the balloon shown partially expanded). Each of the segments 98a, 98b covers the balloon 100 with rip cords 102a, 102b releasing from the center of the balloon. The rip cord 102a from the proximal segment 98a is external to the covered device and the rip cord 102b on the distal segment 98b is threaded through a center lumen 104 of the balloon 100 to aid in release of the distal segment 98b without interference between the rip cord 102b and the expanding balloon 100. By covering an expandable device in this manner it allows the unconstrained expanding device to lengthen axially from its center, allowing for adjustments in the devices length.

Figure 12:
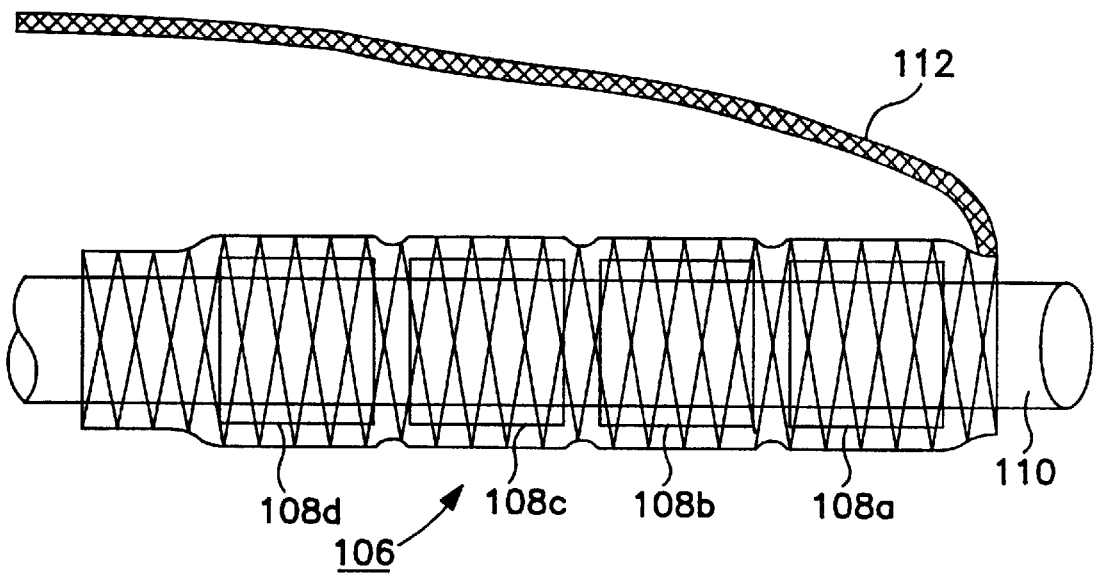
FIG. 12 is a side elevation view of a still further embodiment of a cover of the present invention, this cover surrounding multiple self-expanding devices to be deployed in sequential fashion.

The embodiment illustrated in FIG. 12 is a cover 106 surrounding multiple expanding devices 108a, 108b, 108c, 108d to be deployed in a sequential fashion. This construction allows a catheter 110 to be moved into a first position and a first device 108a can then be deployed by pulling rip cord 112 just enough to release the first device 108a. The catheter 110 can then be repositioned for deployment of the second device 108b. The process can be repeated, deploying each of the devices sequentially, until each of the devices 108 has been deployed. It should be appreciated that multiple devices 108 may also be deployed at one position using this same construction.

Figure 13:
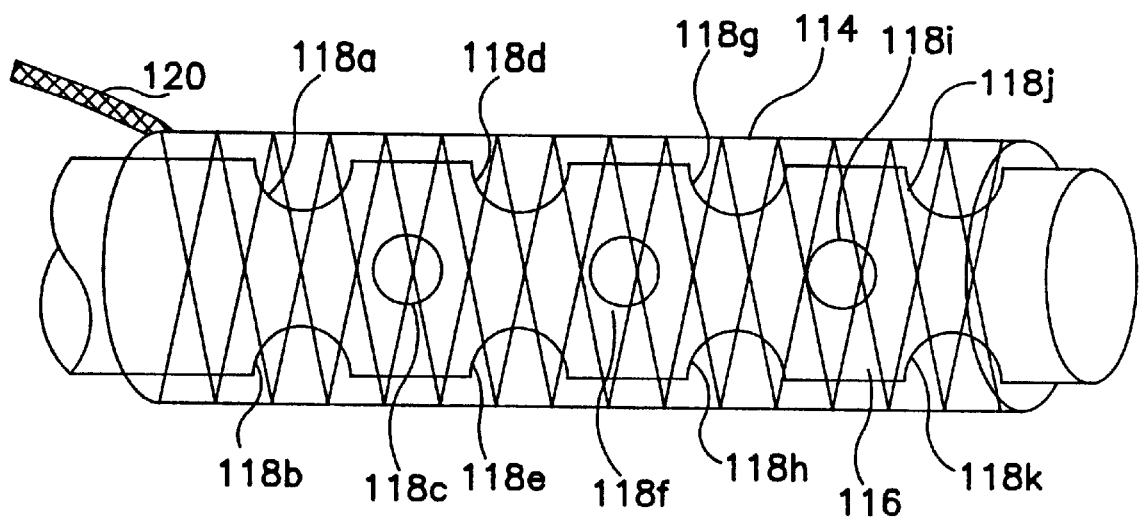
FIG. 13 is a side elevation view of yet another embodiment of a cover of the present invention, this cover comprising a means to provide a drug infusion catheter with variable fluid resistance (the cover being shown with reduced cover density to show details of the covered infusion catheter)

Still another embodiment of the present invention is shown in FIG. 13. In this embodiment, a cover 114 is placed over a drug infusion catheter 116. The cover 114 should be sufficiently dense (that is, with a coverage of 60 to 100% or more) that it will reduce or eliminate liquid passage through the cover when it is in place. The drug infusion catheter 116 is filled or coated with some therapeutic substance and has multiple openings 118a, 118b, 118c, 118d, 118e, 118f, 118g, 118h, 118j, 118k through which the therapeutic substance may permeate into a patient. By covering this catheter 116 with a dense cover 114 of the present invention, a medical professional can use rip cord 120 to remove only enough of the cover 114 to expose a pre-determined number of openings 118. In this way, the amount of drug release can be tightly controlled as to location and/or amount. As was taught with respect to the embodiment of FIG. 12 discussed above, this embodiment of the present invention may dispense therapeutic substances at different locations by simply stripping off more and more of the cover at each new location and/or by being repeatedly repositioned in a patient.

Figure 14:
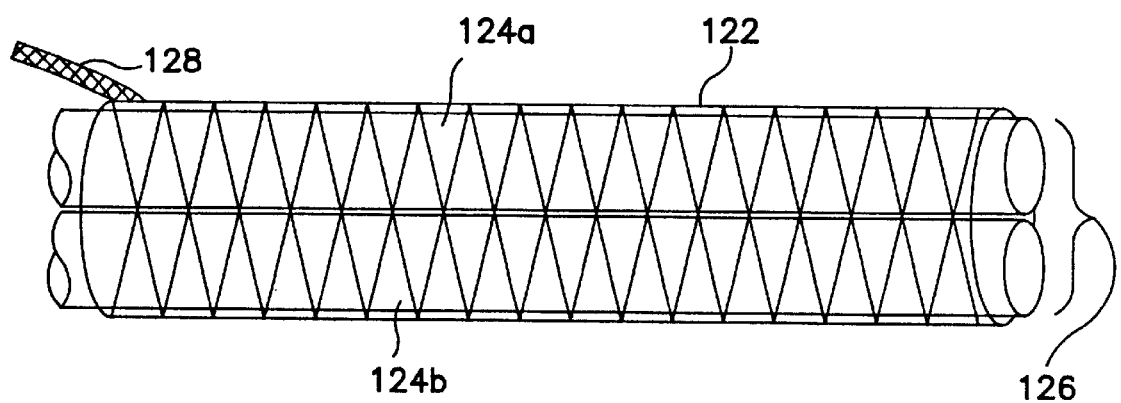
FIG. 14 is a side elevation view of a still further embodiment of a cover of the present invention, this cover attaching together multiple tubes of a multiple lumen catheter.

FIG. 14 shows a cover 122 of the present invention that attaches together multiple tubes 124a, 124b of a multiple lumen catheter 126. This allows the multiple lumen catheter 126 to be initially manipulated through a patient as a single unit and then separated as needed using rip cord 128. One tube may also serve as a guide wire lumen, allowing it to be removed with the other tube left in-situ. This permits the guide wire to be freed for use by an additional catheter.

Figure 15A:
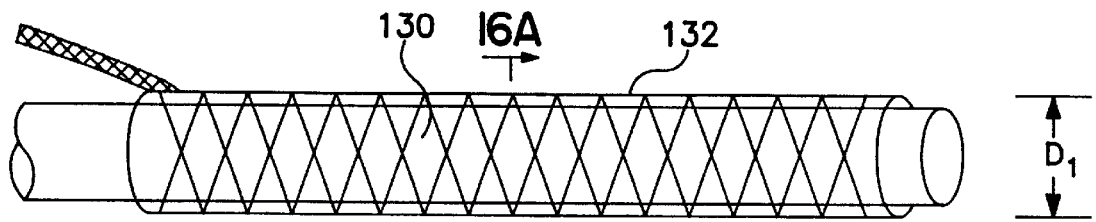
FIGS. 15A through 15C are side elevation views of a cover of the present invention comprising a removable cover for an adjustable diameter balloon, illustrating the process of inflating the balloon within the constraints of the cover and removal of the cover.
Figure 15B:
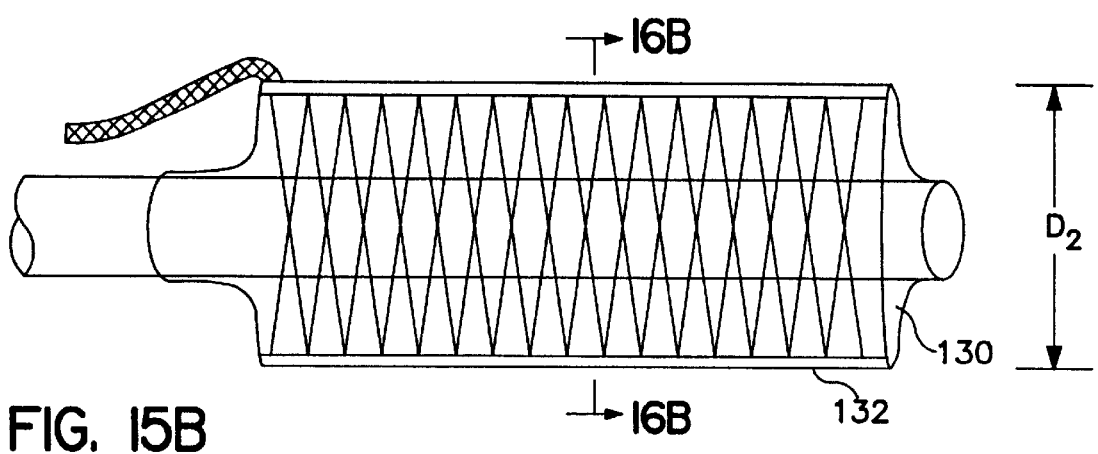
Figure 15C:
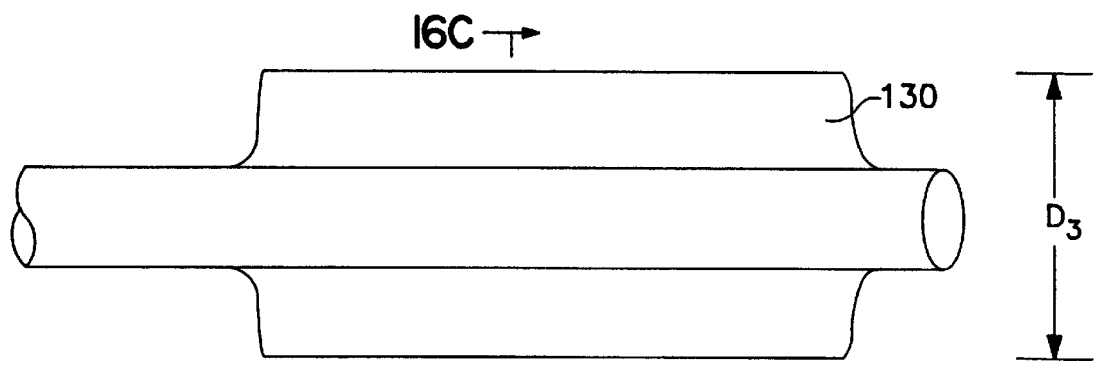
Figure 16A:
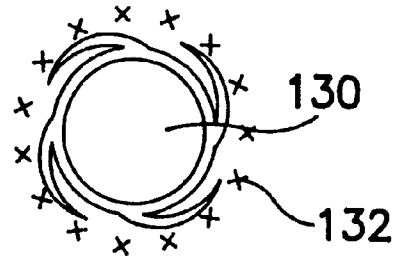
FIGS. 16A through 16C are cross-section views along lines 16A—16A, 16B—16B, and 16C—16C, respectively, of FIGS. 15A through 15C.
Figure 16B:
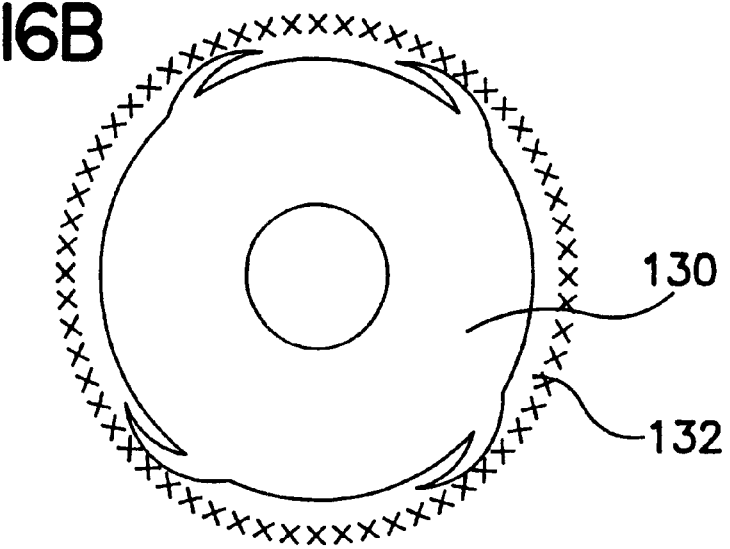
Figure 16C:
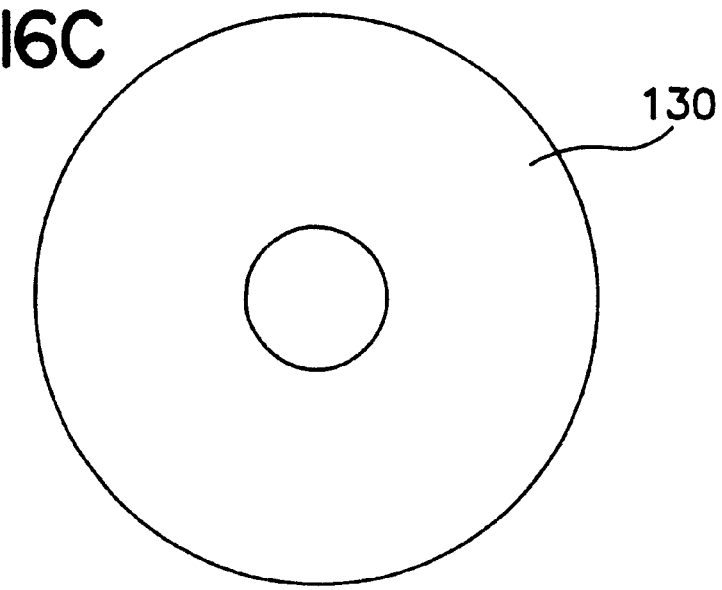

FIGS. 15A to 15C and 16A to 16C illustrate the process of inflating a balloon 130 within the constraints of a removable cover 132 of the present invention. In this instance, the cover is knitted on the balloon in a radially loose configuration. As should be appreciated from these drawings, the cover 132 provides a smooth outer surface within which to almost fully expand the balloon 130 (to diameter $D_2$). Once the balloon 130 is inflated, the cover 132 can then be removed, allowing the balloon 130 to fully expand (to diameter $D_3$ i.e., $D_3 > D_2$) and leaving the uncovered balloon as illustrated in FIGS. 15C and 16C. This method of balloon deployment has a number of advantages over balloon deployment without a cover, including: allowing one balloon to have two separate high pressure inflation diameters; making the balloon more resistant to puncture while covered by the removable sheath; and allowing the balloon to be used at higher pressures than would otherwise not be tolerated by the balloon material alone.

Alternatively, a similar effect may be achieved through use of two or more concentric sheaths, each having slightly larger diameters. Additionally, the cover layers may be adapted to be removed in different orders to achieve different desired results.

One possible means for easing rip cord manipulation is illustrated in FIG. 17. In this embodiment, a multiple lumen catheter 134 is employed with a rip cord 136 of the cover 138 of the present invention being threaded through one lumen 140 of the catheter. In this manner, the rip cord 136 and cover 138 can be easily removed through the catheter lumen 140 without abraiding against a vessel wall. This embodiment is believed to be particularly beneficial where a device is being deployed through a particularly tortuous vessel or other problem area where snagging or other restrictions might be encountered.

Figure 18:
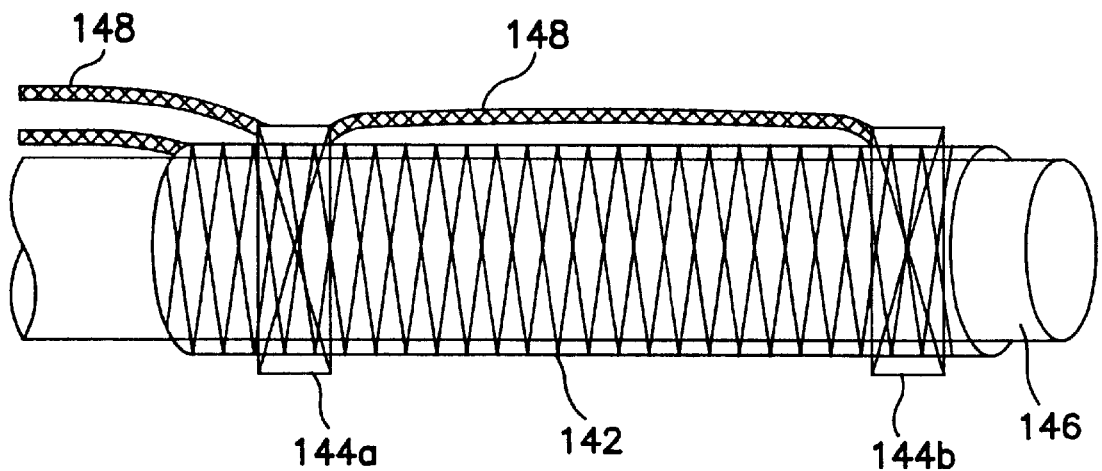
FIG. 18 is a side elevation view of a further embodiment of a cover of the present invention, one of the covers comprising a removable radio opaque knit for use in positioning the covered device.

In the embodiment of FIG. 18, a cover 142 is illustrated that employs a radio opaque knit 144a, 144b for use in fluoroscopic positioning of a covered device 146. In this instance, the radio opaque braid 144 has its own rip cord 148 to allow it to be separately removed from the cover 142. Elements 144a and 144b may be positioned, for instance, to mark each end of the device to be delivered.

Figure 19:
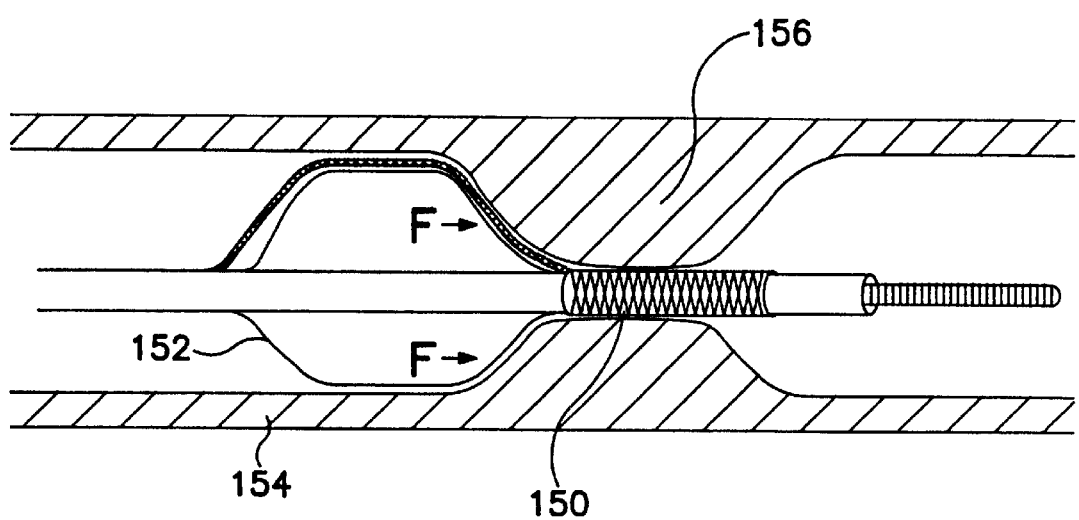
FIG. 19 is a side elevation view of another embodiment of a cover of the present invention, the cover positioned on a balloon to perform an angioplasty by shearing the vessel wall in addition to radially compressing the obstruction in the artery.

In the embodiment shown in FIG. 19, a cover 150 is positioned on a balloon 152 to perform an "extrusion angioplasty" within a blood vessel 154. The process of an "extrusion angioplasty" is designed to augment traditional compressive angioplasty methods employed to remove or remodel a stenotic lesion 156 or other blockage. In addition to providing a radial force, the balloon extrusion angioplasty also creates a "wave" of shear forces (F) that exert complex stresses that can push the blockage along the vessel wall, thus reducing its size or stenotic effect and/or moving it to another portion of the blood vessel. By using the cover 150 of the present invention and releasing it along the length of the balloon 152 in the manner shown, the desired shear forces (F) can thus be generated to remodel the lesion within the blood vessel. This technology may also be used for thrombectomy balloons.

Figure 20:
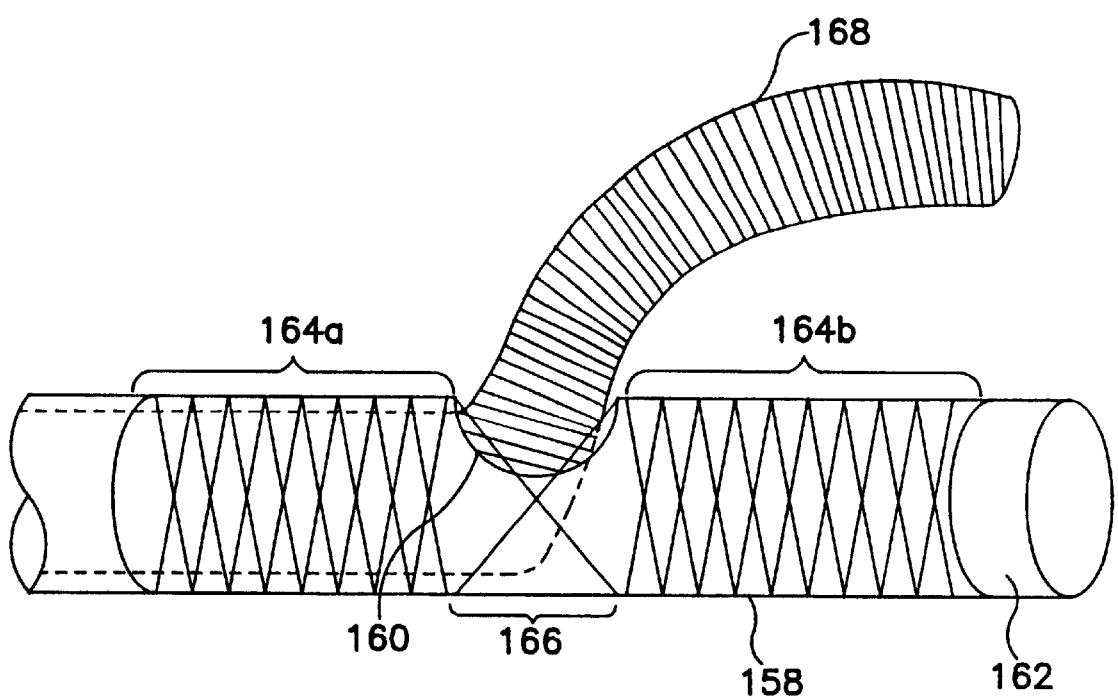
FIG. 20 is a side elevation view of a further embodiment of a cover of the present invention, the cover comprising a variable density knit with a hole in the side of a covered catheter.

A cover 158 of the present invention shown in FIG. 20 comprises a variable density knit with an opening 160 in the side of a covered catheter 162. By providing the cover with dense segments 164a, 164b and open segment 166, this allows passage of a guide wire 168 or other appendage through the cover and opening 160 into or out of the catheter 162.

Figure 21:
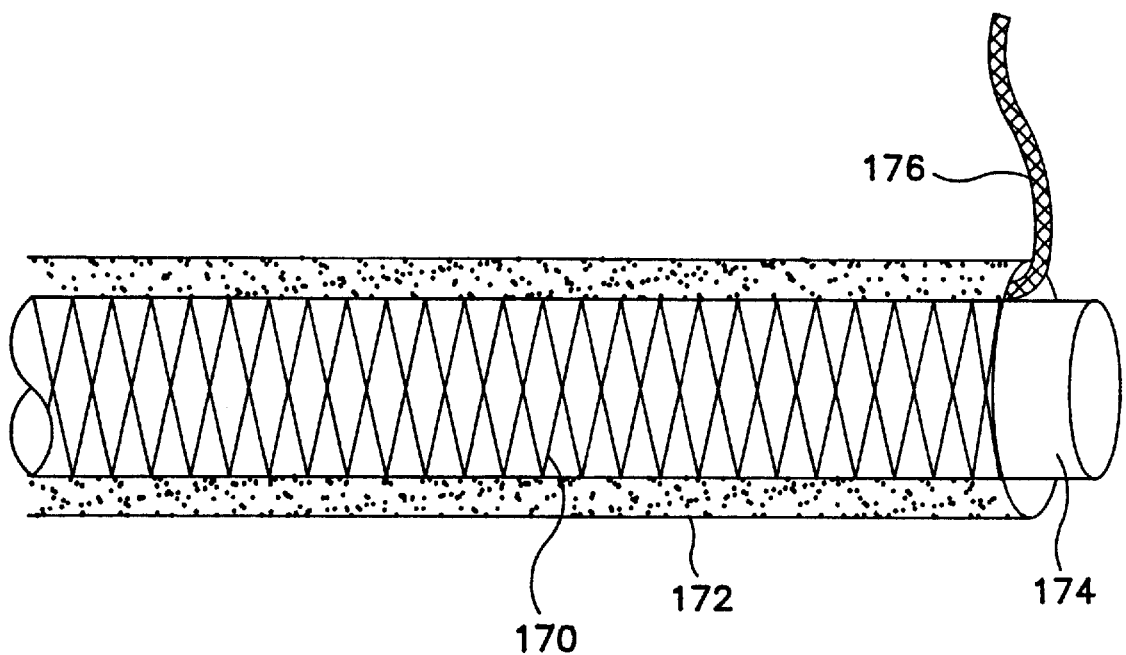
FIG. 21 is a side elevation view of an embodiment of the present invention illustrating a non-medical use of the cover of the present invention, in this instance the cover comprises a readily strippable electrical wire insulation.

The present invention may also have many non-medical uses. For example, illustrated in FIG. 21 is a cover 170 mounted under or imbedded in an insulated jacket 172 over an electrical conductor 174. By pulling on rip cord 176, the jacket and insulation may be readily stripped from the conductor 174 to any desired degree. If desired, once the jacket 172 is correctly positioned, the rip cord 176 may then be cut and sealed to prevent further stripping of the insulation.

Figure 22:
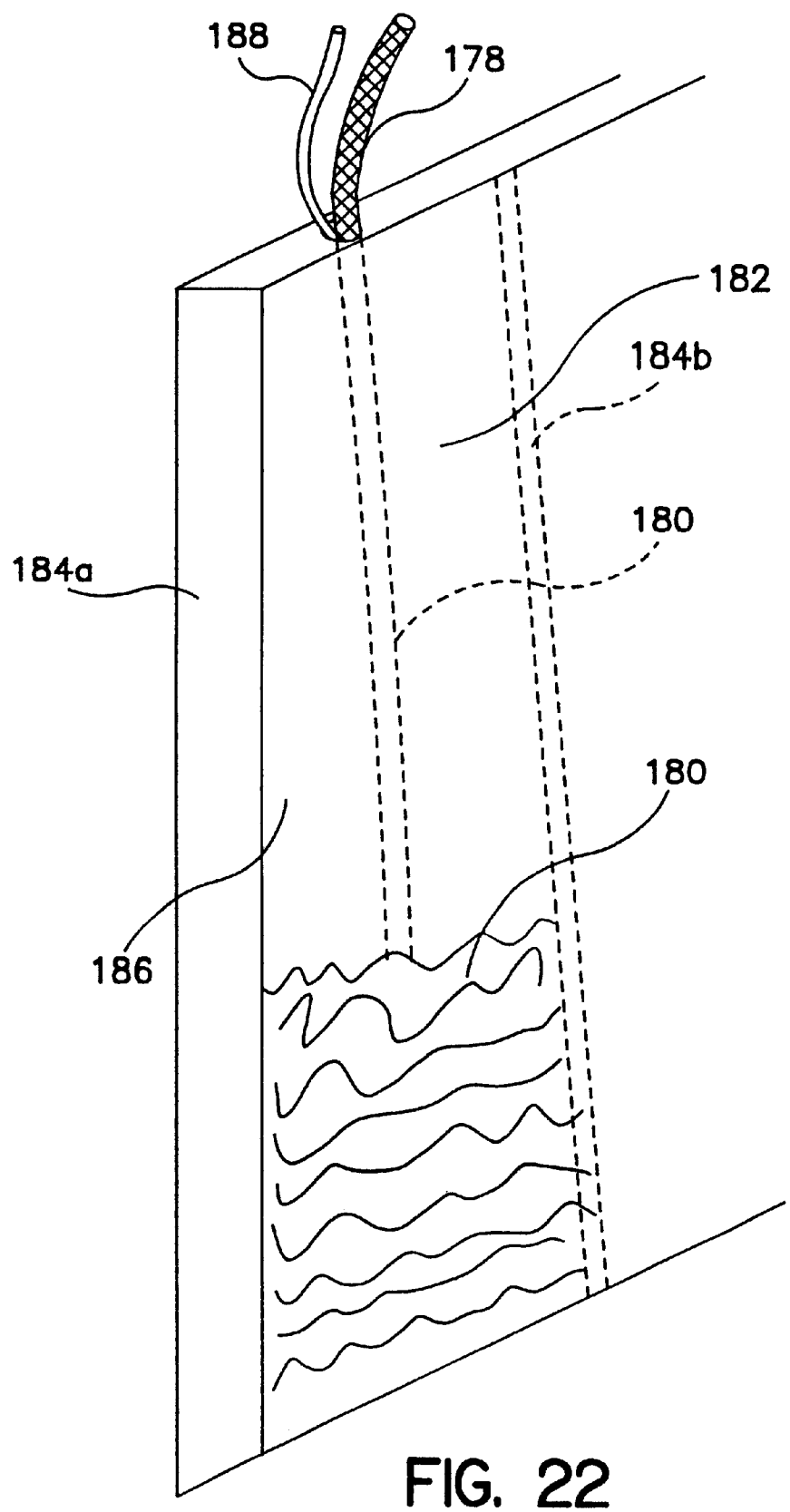
FIG. 22 is a three-quarter isometric view of an embodiment of the present invention wherein the cover used to cover self-expanding insulation and the insulation is being deployed within a contained space.

Another possible non-medical use is shown in FIG. 22. In this instance, a cover 178 is used to contain self-expanding insulation 180, such as foam or fiberglass insulation. When placed into a confined space 182, such as between studs 184a, 184b in an existing wall 186, the cover 178 can be removed using rip cord 188 to permit the insulation to be expanded in place. As compared to existing insulation installation methods, this process permits far better placement of the insulation and far less mess in the process of insulating existing structures.

It should be evident from these two examples that many non-medical applications for the present invention may be possible.

Figure 23A:
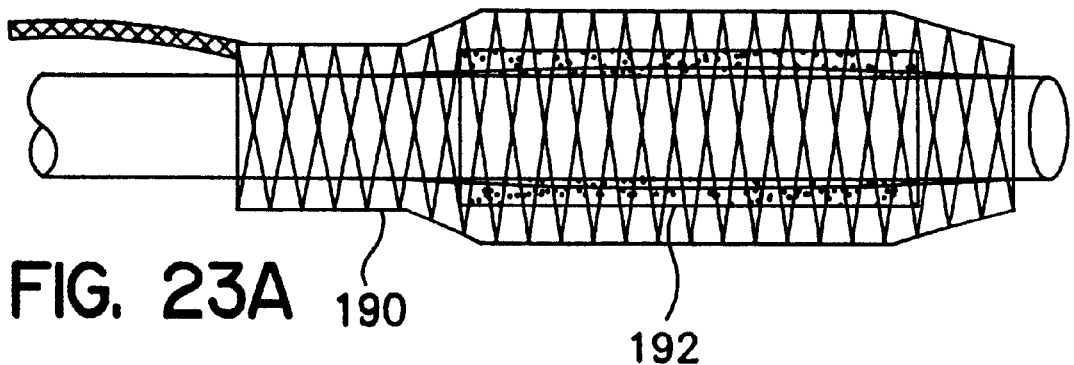
FIGS. 23A through 23C are side elevation views of a cover of the present invention comprising a removable delivery sheath for a plastically deformable device, illustrating the process of inflating the plastically deformable device.
Figure 23B:
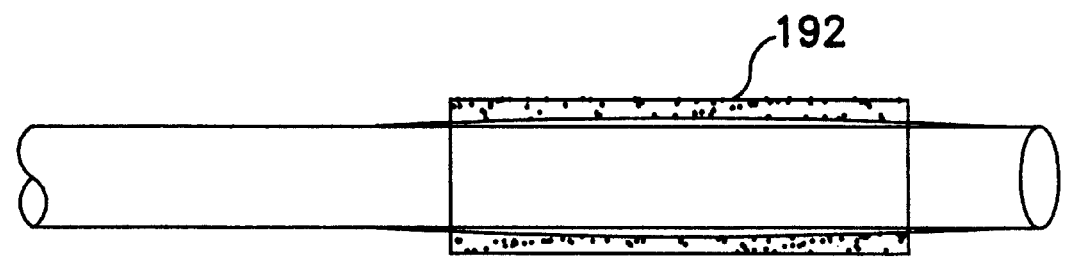
Figure 23C:
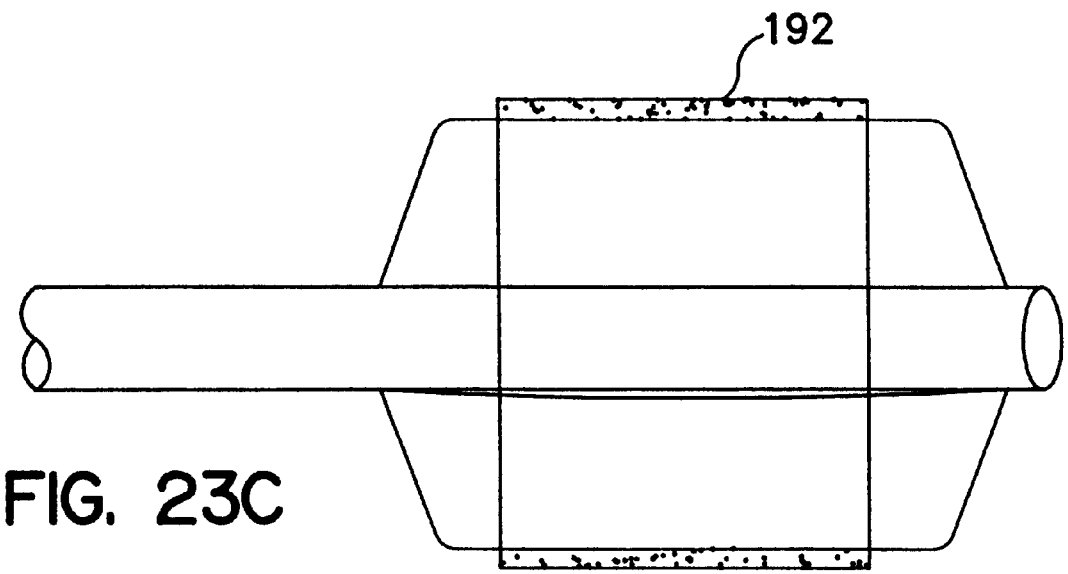

Another medical use of the present invention is shown in FIGS. 23A through 23C. In this instance, a cover 190 of the present invention is used as a delivery sheath for a non-self expanding (that is, a plastically deformable) device 192, such as a Palmaz-Schatz® stent available from Johnson & Johnson. This plastically deformable device is deployed through the following steps:

1. The catheter is manipulated into place with the cover 190 protecting dislodgment of the therapeutic device 192 from the catheter (e.g., angioplasty device);
2. The cover 190 is removed;
3. The device 192 is delivered. (e.g., the angioplasty catheter is inflated.)

Without intending to limit the scope of the present invention, the following examples illustrate how the present invention may be made and used:

EXAMPLE 1

Knit Braid Over an Angioplasty Catheter

A filament is wound in a knit-braid configuration over a Cook (Cook Incorporated, Bloomington, Ind.) Accent® 7 mm×4 cm Balloon Dilatation Catheter. A tubular knit braider by Lamb Knitting Machines (Lamb Knitting Machine Corporation, Model #2NBA/Z-TB Knit Braider, Chicopee, Mass.) is set up to produce a 4 filament warp knit. This machine is modified, with the AC drive motor replaced with a variable speed DC motor (also available from Lamb Knitting Machine Corporation). An eight needle, small bore knitting head is mounted, and every other needle removed, resulting in four needles remaining. Thin, expanded polytetrafluoroethylene (ePTFE) film (produced in accordance with U.S. Pat. No. 3,953,566 to Gore) is slit to achieve four 0.25" (0.64 cm) width sections of film. The film has a thickness of about 0.02 mm, a density of about 0.2 g/cc, and a fibril length of about 70 micron. Thickness may be measured using a snap gauge (such as, a Mitutoyo Snap Gauge, Model 2804-10); density may be calculated based on sample dimensions and mass; and fibril length may be determined by taking a representative scanning electron micrograph (SEM) of the material and measuring average fibril lengths between adjacent polymeric nodes within the material.

Each of these fibers are threaded through separate spring tension devices, through the shuttle guides, through the needles, and pulled through the bottom cylinder. The four filaments are knotted together below this cylinder, and a 72 gram weight is hung from the knot. This machine construction is illustrated in FIG. 6, as previously described.

The crank is slowly turned by hand and the fibers begin to be knit braided. The machine is adjusted (i.e., the needles lowest travel point is adjusted to approximately 1 mm below the needle holding cylinder) to achieve a tight weave. The motor is then turned on, adjusted to a slow rate (of approximately two knits per second), and the machine allowed to knit braid automatically. After approximately 5 cm of length of cover has been knit braided and the machine is running smoothly, the tip of the balloon catheter may be threaded through the top bore on the machine such that the machine starts to knit braid on the distal tip of the catheter toward its hub. The machine will automatically knit-braid until about 5 cm past the balloon of the catheter before the knit braiding operation is ceased. The filaments are then cut at the end of the knit.

Next, 3 of the 4 filaments of the 5 cm length of knit braid past the balloon of the catheter is pulled at a 90° angle from the end of the catheter. With the braid and catheter in this position, a single filament is cut on the catheter on the opposite side from the position of the knit. The knit is further tensioned and this allows the knit on the catheter to unfurl.

This cover over the balloon may then be tested. The catheter diameter may be measure using calipers (Mitutoyo, Model CD-6" BS, Japan). A catheter made through this method has a diameter of 0.098" (2.5 mm) while the encased section has a diameter of 0.110" (2.8 mm). The cover that had started to unfurl has a maximum diameter of 0.024" (0.6 mm). The balloon is attached to a Merit Medical balloon inflation device (Merit Medical, Basix 25, Salt Lake City, Utah) and inflated to 100 psig (7.03 kg/cm$^2$). The cover prevents the balloon from significantly diametrically expanding. Next, while the balloon is still pressurized, the unfurled cover is attached to a force gauge (Ametek Inc., AccuForce Ill., Hatfield, Pa.). The gauge is pulled toward the hub of the catheter. The portion of the cover over the balloon is unfurled, and the force on the rip cord reaches a maximum pressure of about 1.2 lbf (0.54 kgf) tension. This demonstration shows how a filament casing can withstand high internal pressures, yet only a relatively small amount of force is required to unfurl the casing.

EXAMPLE 2

Knit Braid Over Self Expanding Stent

This example demonstrates how a self expanding stent can be restrained by the knitted cover, and then subsequently deployed by pulling the knitted extension in any direction.

A Lamb Knitting Machine Corporation (Chicopee, Mass.) 2NBA/Z-TB Knit Braider is set up as specified in its instructions to create a 4 feed/4 needle tube product on an 8 needle machine. The knit braid pattern has an adjacent crossover. Four spools of JOHNSON & JOHNSON REACH/EASY SLIDE PTFE Dental Floss (Skillman, N.J.) are obtained. This stretched PTFE dental floss material has a denier of about 920. Each floss strand is threaded into the machine, creating 4 feeds. The four strands are tied in a knot below the loop support spindle, and a 72 gram weight is hung from these strands.

A self expanding stent, a Schneider, Inc. (Minneapolis, Minn.) WALLSTENT 10 mm×40 mm, is placed concentrically outside a 0.092 OD 7233 PEBAX (Elf Atochem, Paris, France) tube extruded by Infinity Extrusion and Engineering (Santa Clara, Calif.). The stent is then radially collapsed by digital pressure, causing the stent length to increase. With the stent collapsed completely around the catheter tubing, thread is used to tie the stent to the catheter at both ends and at the middle of the stent. Digital pressure is then removed. No significant stent radially growth is observed.

The stent assembly is then fed from above into the knit braiding machine. Using the hand crank at the rear of the machine, the needles are slowly moved by cranking clockwise (reference the rear of the machine) to start the warp knitting action. The first loop created by the machine is positioned just to the inside of the tied thread at the lower end of the stent. The machine is manually cranked, as the machine knit braid the length of the stent. Just prior to knit braiding over the middle tie thread, this thread is cut and removed along with the first loop. The knit braiding action is terminated just before the other end of the stent and the last pretied thread loop is removed. The crank is then cranked once in the counterclockwise direction, causing all four threads to disengage from the needles. The threads are then cut just below the shuttle extension, releasing the stent/catheter tubing/knit braid assembly from the machine.

Three of the four threads are then tensioned in a perpendicular direction from the axial axis of the catheter. Once the unfurling is started, the fourth strand is grabbed along with the other three strands, assuring that path around the tubing of the fourth strand does not interfere with the unfurling process. The cover will unfurl when the four strands are tensioned perpendicular or toward either end of the tubing. As the cover unfurls, the stent will self deploy to its full diameter.

EXAMPLE 3
Knit Braid With Nitinol Wire

This example illustrates knit braiding with a wire, showing that this process creates a compression resistant, radioopaque structure.

A knit braider is set up as specified in Example 2, except the strands are substituted with 0.006" (0.2 mm) diameter nitinol superelastic wire [describe & CW and composition) (New England Precision Grinding & Wire Company, Inc., Milford, Mass.). Instead of tying the wires together, after they have been threaded through the knitter, wax coated thread is used to connect the four wires.

A 5 mm diameter stainless steel hollow mandrel is inserted into the machine from above. With the four wires and the mandrel fed into the spindles, an approximately 1.5 inch (3.8 cm) long×0.5 inch (1.3 cm) wide strip of electrical tape is applied to the mandrel fixing the four wires at approximately 90° increments from each other. The warp knitting operation is started by rotating the crank clockwise. The crank is manually rotated, assuring that the latch needles grabbed the appropriate wire each time. If a wire is missed, the wire should be manually placed on the appropriate needle. While warp knitting, manual tension is applied to the wires below the spindle to allow the completed wire loop to travel below the latch needles as the latch needles go up. The warp knitting continues until approximately 5 cm had been knit braided. After stopping cranking, another piece of approximately 1.5 inch (3.8 cm) long×0.5 inch (1.3 cm) wide electrical tape was used to affix the wires to the top end of the mandrel. The four wires are cut at the output to the shuttle, and the mandrel-knit braider wire is removed from the machine.

Soft stainless steel wire is then fixed to ends of the wire knit braid just inside of the electrical tape holding the knitted structure on the mandrel. The electrical tape is then removed, and the four wires on either end are trimmed using wire cutters. The assembly is then placed in a oven set to 530° C. for 60 minutes. After this time, the assembly is removed using tongs from the oven and immediately quenched in a room temperature water bath. The knit-braid is then removed from the mandrel by cutting the wire that is fixing the ends and then sliding the knit-braid from the end of the mandrel.

The resulting wire knit braid is stable in its knit-braid form, and demonstrates significant radial compressive resistance to digital pressure. With the braid mounted on a tube, the wires can be removed by initially tensioning 3 of the 4 wires as described in previous examples.

EXAMPLE 4
Knit Braid Over Angioplasty Catheter

This example demonstrates the placement of a cover of the present invention over a angioplasty catheter and the cover's ability to resist radial dilation.

A knit braider is set up as specified in Example 2, except the strands are substituted with nylon sewing thread (Upholstery Home Dec. Super Strong Machine & Hand Sewing thread, Coats & Clark, Inc., Greenville, S.C.). The four threads are threaded into the machine and tied together below the spindle body. The 72 gram weight is then hung from this knot.

A Cook Accent Angioplasty Catheter (8 mm×4 cm, Bloomington, Ind.) is obtained and a vacuum is drawn in the balloon by attaching a syringe to the balloon lumens luer lock and retracting its plunger. While maintaining the vacuum, the catheter is fed from below into the spindle, past the needle, and into the shuttle body. The knit braiding operation is commenced by cranking the crank clockwise, and the knitting starts 8 cm proximal to the balloon. The cranking continues until the knit braid continues about 10 cm past the distal tip of the catheter. After stopping the crank, the four threads are severed at the shuttle and the catheter is removed from the machine. The syringe is then detached from the balloon luer lock connector.

One thread of the four is then severed right on the distal tip of the catheter. The 10 cm extension of the braid is then tensioned, and the knit-braid starts to unfurl proximally toward the balloon and hub of the catheter. A syringe is reattached to the balloon lumens luer lock. Approximately 5 atm pressure is applied to the balloon. The balloon resists significant dilatation from its collapsed state, and the braid does not unfurl.

Among the advantages of the cover of the present invention are: the knit-braid will retain high internal pressures with minimal radial growth; very low forces are required to unfurl the knit-braided cover; the rip cord can be pulled from any direction to unfurl the knit-braid cover; because the rip cord is knitted, and multi-filamented, the rip cord has high strength; with multiple strong filaments, only thin casings are needed, typically adding less than 1 French to the across-section of the delivery catheter; also with strong filaments, the cross section of the rip cord is small; the cover can be unfurled in a controlled fashion and controlled rate; the knit can be employed to fully encase the expandable device; the knit is 100% removable along a single vector, leaving only the expandable device in place and minimizing potential embolization and/or vascular trauma. The entire cover can be constructed from a single material (or multiple materials, as desired), allowing, for example, a cover constructed entirely from PTFE; no weaving through structure of the expandable device is required; almost any shape of collapsed device can be encased, with the outer surface made relatively smooth with the cover of the present invention; the cover is very flexible, adding minimal stiffness to the delivered device; the knit can be applied sequentially over different areas, allowing for a multi stage deployment, and allowing the ends of the stent to be deployed before the center, an outer covering to be released before the inner covering, etc.; the "density" of the knit can be varied, allowing a branch or a guide wire to exit from the side of the knit; the cover is easy to manufacture and can be easily automated; during manufacturing, the knitting process supplies some radial inward forces to the expandable device, potentially decreasing its profile further; the knit allows for use of either films or fibers; the rip cord is significantly longer than the length of the knitting being "opened," allowing for precise deployment of the expandable device; and the deployment line pull length to deployment length ratio can be adjusted by varying the circumferential length of the narrowest knit.

Other advantages of the present invention include: the cover provides a relatively uniform distribution of compression over the external surface of the constrained device; by extending the cover beyond the end of a covered prosthesis or the like, a smooth transition of profile between the catheter shaft and device can be established; and the cover can be used to modify the flexibility of a delivery system by changing degree or type of coverage.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A removable cover mounted over a medical device comprising a plurality of filaments;

the filaments being attached together to form a multi-filament interlocking structure covering the device;

a rip cord comprising ends of each of the filaments;

wherein the interlocking structure separates from the device with two of the plurality of filaments disconnecting from each other in an essentially straight line when tension is applied to the rip cord.

2. The cover of claim 1 wherein the rip cord comprises a multiple-filament interwoven rip cord.

3. The cover of claim 1 wherein the filaments are interwoven as a warp knit.

4. The cover of claim 1 wherein the rip cord removes all of the filaments from the device in an essentially straight line.

5. A removable cover mounted over a medical device comprising a plurality of filaments;

the filaments being attached together to form a multi-filament interlocking structure covering the device;

a rip cord comprising ends of each of the filaments;

wherein the interlocking structure separates from the device with the rip cord removing all of the filaments from the device in an essentially straight line when tension is applied to the rip cord.

6. The cover of claim 5 wherein the rip cord comprises a multiple-filament interwoven rip cord.

7. The cover of claim 5 wherein the filaments are interwoven as a warp knit.

8. The cover of claim 5 wherein two of the plurality of filaments disconnect from each other in an essentially straight line when tension is applied to the rip cord.

9. A removable cover mounted over a medical device comprising a plurality of filaments;

the filaments being attached together to form a multi-filaments interlocking structure covering the device;

ends of each of the filaments interwoven together to form a multi-filament rip cord;

wherein the interlocking structure separates from the device when tension is applied to the rip cord.

10. The removable cover of claim 9 wherein the interlocking structure separates from the device with the rip cord removing all of the filaments from the device in an essentially straight line when tension is applied to the rip cord.

11. The cover of claim 9 wherein the filaments are interwoven as a warp knit.

12. The cover of claim 9 wherein two of the plurality of filaments disconnect from each other in an essentially straight line when tension is applied to the rip cord.

13. The cover of claim 9 wherein the cover comprises a variable density knit.

14. The cover of claim 5 wherein the cover comprises a variable density knit.

15. The cover of claim 1 wherein the cover comprises a variable density knit.

* * * * *